United States Patent
Poncelet et al.

(10) Patent No.: US 6,656,439 B2
(45) Date of Patent: *Dec. 2, 2003

(54) PILLARED TRIOCTAHEDRAL MICAS AND/OR VERMICULITES

(75) Inventors: Georges Poncelet, Brussels (BE); Francisco Del Rey, Almeria (ES)

(73) Assignee: Université Catholique de Louvain, Louvain-la-Neuve (BE)

( * ) Notice: Subject to any disclaimer, the term of this patent is extended or adjusted under 35 U.S.C. 154(b) by 145 days.

This patent is subject to a terminal disclaimer.

(21) Appl. No.: 09/802,307

(22) Filed: Mar. 8, 2001

(65) Prior Publication Data

US 2003/0201206 A1 Oct. 30, 2003

Related U.S. Application Data

(63) Continuation of application No. 09/366,030, filed on Aug. 2, 1999, now Pat. No. 6,300,269.

(30) Foreign Application Priority Data

Jul. 31, 1998 (EP) .............................................. 98870169

(51) Int. Cl.[7] .............................. B01J 29/03; B01J 21/12
(52) U.S. Cl. ........................ 423/239.1; 502/63; 502/84; 585/250
(58) Field of Search ..................... 502/63, 84; 585/250; 423/235, 239.1

(56) References Cited

U.S. PATENT DOCUMENTS

| | | | |
|---|---|---|---|
| 4,510,257 A | 4/1985 | Lewis et al. | 502/63 |
| 5,017,537 A | 5/1991 | Clearfield | 502/62 |
| 5,200,378 A | 4/1993 | Clearfield | 502/63 |
| 5,330,734 A | 7/1994 | Johnson et al. | 423/328.3 |
| 5,340,657 A | 8/1994 | Kerby et al. | 264/110 |
| 6,300,269 B1 * | 10/2001 | Poncelet et al. | 502/63 |

FOREIGN PATENT DOCUMENTS

| | | | | |
|---|---|---|---|---|
| EP | 0 240 359 B1 | 4/1987 | | C01B/33/26 |
| WO | WO 88/00091 | 1/1988 | | B01J/21/16 |
| WO | WO 96/07613 | 3/1996 | | C01B/33/40 |

OTHER PUBLICATIONS

"Partial Pillaring of vermiculate by aluminum polycations" Michot et al. Clay Miner.29(1) 1994. pp. 133–136.

* cited by examiner

Primary Examiner—Stanley S. Silverman
Assistant Examiner—Maribel Medina
(74) Attorney, Agent, or Firm—Knobbe, Martens, Olson & Bear, LLP

(57) ABSTRACT

Pillared trioctahedral micas and/or vermiculites are prepared. The process includes a conditioning operation for the partial reduction of the layer charge through an accelerated weathering process, and also includes a pillaring operation.

10 Claims, 10 Drawing Sheets

PILLARED TRIOCTAHEDRAL MICAS AND/OR VERMICULITES

RELATED APPLICATION

This application is a continuation of prior application Ser. No. 09/366,030, filed Aug. 2, 1999 now U.S. Pat. No. 6,300,269.

FIELD OF THE INVENTION

The present invention is related to pillared trioctahedral-type natural micas and vermiculites, to a preparation method thereof, and to their applications.

BACKGROUND OF THE INVENTION

1. Technical Background of the Invention

Pillared interlayered smectites (PILCs) with a large variety of pillars have been described in the scientific literature (journals, patents), among which the Al-pillared clays are the most documented ones. Similar materials with pillars based on other elements such as Zr, Cr, Ti, Si, Fe, Ga, Si, Ta, V, Mo, Nb, combinations of two or more of these elements or combinations of one or several of those elements with others elements not mentioned above (as e.g. Ni, Cu, Co, etc.), rare-earth (La, Ce . . . )-containing pillars have been successfully prepared and reported in the literature. Pillared clays containing two or more elements in the pillars are also named mixed pillared clays.

Pillared clays show interesting potentialities in catalysis, as catalysts or supports to catalytic phase(s) or in admixture with other catalysts or catalyst components (e.g. zeolites, metal oxides, etc.), especially as catalysts for e.g. hydrocarbons transformation. Pillared materials also find potential interest as adsorbents and in other domains such as in gas separation processes; as scavengers for heavy metals (treatment of waste water); in $SO_2$ and $NO_x$ abatement; in purification of edible oil, cation selective composite membranes; as solid electrolytes; as host materials for (conducting) polymers; etc.

Trioctahedral Micas

Trioctahedral micas refer to layered 2:1 sheet (or lamellar) silicates in which the octahedral layer is sandwiched between two adjacent tetrahedral layers and mainly contains divalent cations with the results that all the possible octahedral positions are occupied. They differ from dioctahedral micas (muscovite-type), where ⅔ of the octahedral positions are filled with mostly trivalent cations. The general formula of the end-member phlogopite mineral is $K_2Mg_6(Si_6Al_2)O_{20}(OH,F)_4$. The structural substitutions mainly occur in the octahedral layers but also in the tetrahedral ones and are responsible for the wide range of chemical compositions of the trioctahedral micas. The high number of substitutions is at the origin of the high net negative layer charge in micas. Potassium is usually the dominant interlayer cation ensuring electroneutrality of the layers. Trioctahedral micas may contain substantial amounts of fluorine (replacing structural hydroxyls) which conveys resistance to weathering, hardness and thermal resistance. The principal cations in the octahedral layer of natural trioctahedral micas are $Mg^{2+}$, $Fe^{2+}$, $Al^{3+}$ and $Fe^{3+}$, with smaller proportions of $Mn^{2+}$, $Ti^{4+}$ and $Li^+$. Phlogopites refer to trioctahedral micas in which more than 70% of the occupied octahedral sites contain $Mg^{2+}$, whereas biotites define the micas where 20 to 60% of these sites are $Mg^{2+}$ [Newman & Brown, in Chemistry of Clays and Clay Minerals, A. C. D Newman (Ed.), Mineralogical Soc. 6, Longman, 1987, p. 75]. The potassium ions located between the unit layers just fit into hexagonal cavities (perforations) in the oxygen plane of the tetrahedral layers. Adjacent layers are stacked in such a way that the potassium ion is equidistant from 12 oxygens, 6 of each tetrahedral layer [R. E. Grim, Clay Mineralogy, McGraw-Hill, 1953, p.65]. In their original state, natural micas do not swell in the presence of water or polar solvents because the hydration energy of the interlayer potassium ions is insufficient to overcome the co-operative structural forces at the coherent edges of a cleavage surface [Newman & Brown, Nature 223, 175, 1969].

The absence of swelling properties of natural micas makes it impossible, without modifying the mineral, to obtain pillared intercalated forms equivalent to those readily obtained with swelling clays (smectites) in which the clay sheets are separated from each other by pillars of inorganic nature, which confer to these materials thermally resistant structural and textural characteristics such as permanent elevated spacings, high specific surface area and micropore volume, and surface properties (acido-basic, redox).

Vermiculites

Vermiculites belong to a group of hydrated aluminium silicates. These minerals may be considered as "swelling trioctahedral micas" containing Al-for-Si substitutions in the tetrahedral layers (as in micas), and Al-, Fe-, and Ti-for-Mg substitutions in the octahedral layers. Because of both types of substitutions, the overall negative charge of the structure results, as in micas, from an imbalance between the negative charge of the tetrahedral layer and the excess positive charge of the octahedral layer. As in micas and smectites, the excess negative charge is counterbalanced by cations located in the region between adjacent sheets which ensure electroneutrality of the layers. Most often, the interlayer cations are magnesium ions. The layer charge densities in vermiculites are intermediate between those of micas and smectites. Unlike micas, vermiculites may swell and the layers may expand when polar molecules are introduced in the interlamellar region but this swelling capability is much reduced compared with smectites. The interlayer charge balancing cations (magnesium ions) are exchangeable.

Vermiculites (and a fortiori micas) could not be intercalated with bulky poly-hydroxy-aluminum species to form a pillared material exhibiting spacings of about 17–18 Å (gallery height of about 8 Å) as in pillared smectites, a failure which has been attributed to the high layer charge density of these minerals. Contacting vermiculite suspensions with $Al_{13}$-containing pillaring solutions led to expanded materials exhibiting only about 14 Å spacings [references 1–7]. Taking advantage of the high spacings (27–28 Å) developed upon adsorption of long chain amines and alcohols to introduce Al pillars was unsuccessful [reference 5]. Preliminary dealumination of vermiculite by treatment with an aqueous solution of $(NH_4)_2SiF_6$ followed by the addition of the pillaring solution did not result in materials with improved spacings [reference 7]. A mixture of a pillared fraction of vermiculite (with 18 Å spacing stable at 500° C.) and of unpillared fraction was obtained upon contacting with $Al_{13}$-containing solutions a suspension of vermiculite that was previously treated with L-ornithine [reference 8]. However, repeated attempts to reproduce the method were unsuccessful.

2. State of the Art

The documents U.S. Pat. Nos. 5,200,378 and 5,017,537 are concerned with the pillaring of synthetic layered phosphates. Layered phosphates have nothing in common with natural micas. The intercalation is performed after a previous intercalation of an amine (amide or dimethyl sulfoxide)

in order to expand the interlayers. Attempts to pre-swell vermiculite with a long chain amine or alcohol and to treat the expanded vermiculite with a pillaring solution did not allow to obtain 18 Å Al-pillared vermiculite.

The documents U.S. Pat. No. 5,340,657 and EP-0240359 deal with the Al-pillaring of synthetic sodium tetrasilicic fluor micas which have nothing in common with natural micas. The Na-TSF micas have only octahedral substitutions (Li for Mg or Mg for Al), but no aluminium in the tetrahedral layers. Natural micas have substitutions in both the tetrahedral (Al for Si) and octahedral (Al, Fe for Mg) layers. Na-TSF micas are synthesized in a soda-containing medium (thus no interlayer potassium as in natural micas). The presence of exchangeable Na in the interlayers as charge neutralizing cations confers swelling properties. Natural micas have potassium ions between the layers and do not swell in polar media. Na-TSF micas can be pillared when they are contacted with the pillaring solution. Nothing like occurs when doing so with natural micas. This is the principal reason for the prerequisited conditioning operation of the natural micas (aiming at the charge reduction of vermiculites and micas and conversion to homoionic form of hydrated ions). Synthetic Na-micas have, as hydrothermally synthetic layer materials, very small particle sizes. Particles of the order of 0.1 micron are preferred in the document EP-0240359 (p. 3, lines 8–10).

The document U.S. Pat. No. 4,510,257 describes a method which allows to intercalate three-dimensional silicon oxide pillars from organo-silicon derivatives in the clay interlayers. The material is then calcined to decompose the organic moiety. Vermiculite is mentioned (yet no example of successful Si-pillared material is provided).

The document WO98/00091 deals with the pillaring of synthetic layered silicate materials which have no octahedral layers and are thus different from either synthetic sodium fluor tetrasilicic "micas" or natural micas (as in our patent application), both of which having octahedral layers.

SUMMARY OF THE INVENTION

This invention describes a method for the obtention of pillared trioctahedral-type micas (PILMs) and vermiculites (PILVs) characterised by thermally stable interlayer distances, high specific surface areas and micropore volumes, and acidic properties. These features are similar to those found for equivalent pillared interlayered materials obtained from naturally occurring swelling clays, or smectites, (or their hydrothermally synthesised analogues) such as montmorillonites (bentonites), beidellites, hectorites (fluorhectorite and laponite, synthetic analogues), saponites, nontronites, rectorites (interstratified montmorillonite-muscovite), Ni-SMM and SMM (the so-called synthetic expandable mica-montmorillonite) to quote some of the main ones used in the preparation of pillared interlayered clays (PILCs).

Pillaring is achieved after submitting the starting micas and vermiculites to a conditioning procedure consisting of chemical and thermal treatments which aim to reduce the layer charge density and replace the charge balancing potassium ions located in the interlayers of the initial micas, or the magnesium ions in the case of vermiculites, by hydrated cations such as f.i. sodium ions. The charge reduced cation-exchanged ($Na^+$, $Ca^{+2}$, . . . ) forms of micas and vermiculites may be converted to any other cationic form(s) by simple exchange of the interlayer cations (fi. $Na^+$) by the desired element(s). Pillared micas and vermiculites are obtained by contacting Na-micas and Na-vermiculites with solutions containing the pillaring species, namely, polyoxohydroxy-metal cations which intercalate between the layers according to a cation-exchange process, in a similar manner as for the obtention of pillared smectites. Successful insertion of Al-polymerised species is not restricted to the sole Al element. Substitution of Al in the pillaring solution by any one of the elements indicated below or mixtures thereof which have been successfully employed in the preparation of pillared smectites, give rise to equivalent pillared micas and vermiculites, thus offering materials with a wide variety of intercalated pillars and mixed pillars differing in the nature of the pillaring species and composition.

It is one object of the present invention that the same preparation procedure may be equally applied to trioctahedral micas and vermiculites and wastes thereof (as defined below) to obtain pillared materials exhibiting the characteristic features of analogous materials prepared from smectites.

In accordance with the aforementioned objectives, it is a particular object of the invention to find a new route to the pillaring of trioctahedral micas and vermiculites with solutions containing Al hydroxy-polymeric species often referred to as $AlO_4Al_{12}(OH)_{24}(H_2O)_{12}^{7+}$ (in short, $Al_{13}$) with Keggin-like structure [reference 9]. This objective is realized through the partial reduction of the layer charge density, which may be compared to an "accelerated weathering" process, and through the application of pillaring solutions in the form of partially hydrolysed Al solutions, the Al species in presence in these solutions having been identified [references 9–12].

It is a further object that this invention is not restricted to the sole case of aluminium as the metal element of the pillar since, as stated above, substitution of Al in the pillaring solution by anyone of the elements Zr, Ti, Si, Cr, Fe, Ta, Nb, Ga etc. or combinations of different elements including lanthanides or mixtures thereof give rise to equivalent pillared micas and vermiculites.

Therefore, it is an object of the invention to give access via the successful Al-pillaring of micas and vermiculites to the preparation of materials with different types of pillar species (based, e.g., on Zr, Ti, Si, Cr, Fe, Ta, Nb, Ga, etc, or combinations of different elements, including lanthanides) with possible uses in various catalytic reactions and other application areas.

Further, the greater intrinsic structural stability of micas and vermiculites compared with smectites is of considerable interest in achieving pillared materials which possess improved resistance to thermal treatments, a weakness shared by all smectite-based pillared materials.

Another interest of the method is the possibility to use micas and vermiculites with various particle sizes.

Other objects of the invention include post-exchange and/or impregnation of the pillared materials, improvement of the acidic properties, use in fluidised bed applications.

Further details will appear in the claims and in the description hereafter of preferred embodiments of the invention.

DETAILED DESCRIPTION OF THE INVENTION

General Description of the Pillaring Procedure

Figure 1:
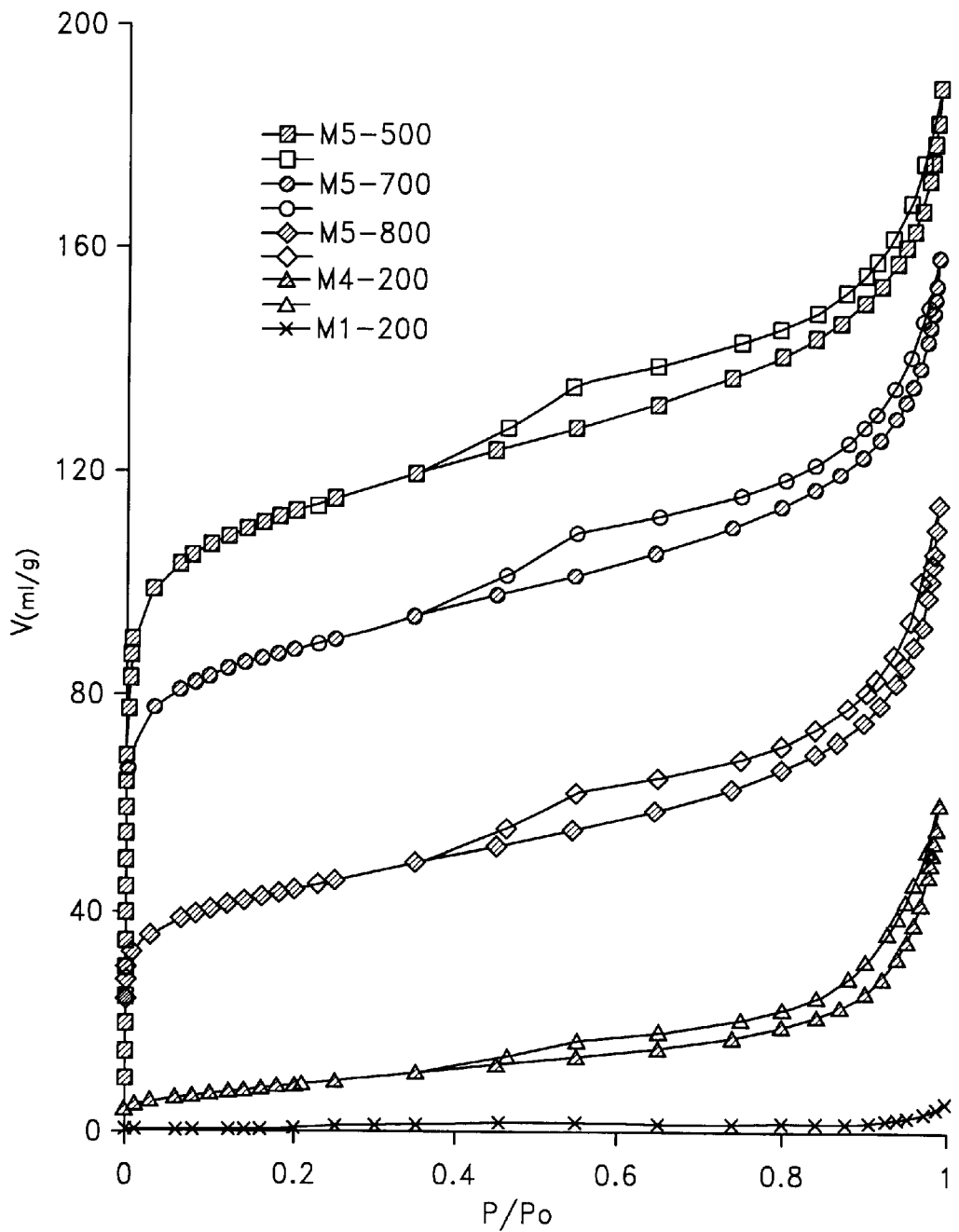
FIG. 1 represents nitrogen sorption isotherms of the starting mica (Mi), of homoionic Na-exchanged mica (M4) and of Al-pillared mica calcined at 500° C. (M5-500), 700° C. (M5-700) and 800° C. (M5-800). Outgassing at 200° C. for 6 h.

Al-pillared micas and vermiculites exhibiting stable spacings (18 Å and more for room temperature dried samples) are obtained after:

i) a conditioning step which brings about a reduction of the layer charge density of the minerals and allows to convert the minerals in fully exchanged monoionic forms and ii) a pillaring step consisting of contacting the cation-exchanged minerals (monoionic forms) with the pillaring solution following any method known from the literature.

Efficient pillaring is achieved provided that the conditioning treatment is properly carried out. Adequate conditioning can be controlled by characterising the solids at the different intermediate steps by use of suitable techniques and methods (e.g. X-ray diffraction, nitrogen sorption isotherms etc.). These controls may require washing and drying operations which are superfluous in the continuous preparation procedure.

In the "standard method", the conditioning step of micas and vermiculites consists of four consecutive operations, prior to the pillaring operation itself. These two aspects will be discussed separately.

Conditioning of the Starting Mica and Vermiculite

The conditioning treatment consists principally of the reduction of the layer charge density of the starting minerals and the replacement of the interlayer potassium ions in the initial mica, and of the magnesium ions and other cations in the case of vermiculites, by hydrated cations (e.g. sodium ions). Conditioning is achieved through the following sequence of treatments: the mineral is first treated with diluted mineral acid, preferably nitric acid. The solid is washed free of excess acid and dissolution products and then calcined at 500–650° C. Thereafter, the solid is preferably leached with a diluted (mineral) acid, and preferably with a complexing (chelating) organic acid. After elimination of the excess complexing agent (or acid) and dissolution debris, the solid is converted to the monoionic form by an usual ion-exchange treatment with a solution of a soluble salt (e.g. of sodium), and washed free from excess salt.

At this stage, the mineral is ready for the pillaring operation. This sequence of treatments is similarly applied to micas and vermiculites (as well as to "wastes" thereof, as defined below). The exact conditions of acid concentration and treatment duration, however, may differ somewhat for a mica and for a vermiculite as it will be illustrated in the following examples.

Pillaring Operation

The monoionic forms of micas and vermiculites ($Na^+$, $Ca^{+2}$, . . . ) are contacted with a solution containing the pillaring species (the pillaring solution). The pillar precursors are introduced in the interlayer space via an exchange process between the charge balancing cations of the minerals obtained at the end of the conditioning operation and the positively charged species present in the pillaring solution. Any known method used for the preparation of pillared smectites may be applied.

DETAILED DESCRIPTION OF THE CONDITIONING TREATMENT

Step 1.—Nitric Acid Treatment

The starting phlogopite or vermiculite was leached with nitric acid solution for 4 hours at 95° C. under stirring, using a concentration of solids between 4 and 20 wt %, typically 10 wt %. The ratio [mol of nitric acid/mass of phlogopite] was included between 0.007 and 0.011 mol $g^{-1}$, typically 0.008 mol $g^{-1}$. The concentration of the acid solution ranged between 0.29 M and 1.44 M, typically 0.78 M.

Step 2.—Thermal Treatment

The sample obtained at step 1 was calcined at 500–700° C., typically at 600° C. for 4 hours under static air.

Step 3.—Treatment With Complexing Agents (Typically Oxalic Acid)

The treatment with a complexing agent mainly aims to remove the species dissolved from the structure in the preceding steps, which are partly present in the interlayers. The conditions were as follows:

Concentration of Solids:
between 2.6 and 10 wt %, typically 10 wt %
Concentration of the Complexing Acid Solution:
between 0.06 M and 0.24 M, typically 0.12 M for 10 wt % of solid
Duration of the Treatment:
micas: between 2.0 and 4 hours, typically 2.5 h
vermiculites: between 0.5 and 2 hours, typically 1 h
Temperature of Treatment:
between 80 and 95° C., typically 80° C.
Alternative (step-3) Treatments:
Citric Acid
Sample obtained at step 2 was leached with a 0.5 M citric acid solution (pH 2.1) at 80° C. for 4 hours.
Concentration of solids between 1.7 and 4 wt %, typically 4 wt %.

Acetic Acid

Sample obtained at step 2 was leached with 0.005 mol acetic acid per gram of clay at 80° C. for 3 hours. Concentration of solids of 7.6 wt %

Hydrochloric Acid

Sample obtained at step 2 was leached with 0.0002 mol hydrochloric acid peer gram solid at 80° C. for 3 hours. Concentration of solids of 7.6 wt %

Step 4.—Sodium Exchange(*)

Concentration of the NaCl solution:

between 1 M and 3 M, typically 1 M.
Concentration of Solids:

between 0.35 and 6.4 wt %, typically 2 wt %.
Number of Exchange Operations:

between 4 and 6, typically 5 for 12 hours each.
Temperature of exchange:

95° C.

At the end of this step, the exchange sites are occupied by sodium ions. Other cationic forms may be obtained by further exchange of the Na-forms with solution(s) of the desired element(s).

(*) Notes:

Any known cation exchange method may equally be used.
Any other salt of hydrated cations instead of a Na salt, and different concentrations of the exchange solution and exchange times may be used.

PREFERRED EMBODIMENTS OF THE INVENTION

1. Pillaring of Micas

Starting Phlogopite

The starting phlogopite-type mica (Siilinjaeervi deposit, Finland) was a micronized grade (particle size: 90% smaller than 40 microns, 50% smaller than 20 microns). Minor amounts of calcite and apatite were identified by X-ray diffraction.

The chemical analysis (by I.C.P.S.) was as follows (in wt % on the basis of samples calcined at 1000° C.).

| $SiO_2$ | $Al_2O_3$ | MgO | $Fe_2O_3$ | $K_2O$ | CaO, NaO, $TiO_2$, $P_2O_5$ |
|---|---|---|---|---|---|
| 41.05 | 9.71 | 23.73 | 7.93 | 9.50 | <6.83 |

Conditioning

The conditioning operation follows the steps as described heretofore.

The exact operating conditions to prepare two batches of Al-pillared micas are given hereafter.

|  | Batch 1 | Batch 2 |
|---|---|---|
| Step 1 |  |  |
| Conc. $HNO_3$ (M) | 0.72 | 0.78 |
| Duration (in h) | 4 | 4 |
| Temperature (° C.) | 95 | 95 |
| Conc. solids (wt %) | 10 | 10 |
| mole $H^+$ $g^{-1}$ solid | 0.007 | 0.008 |

The resulting solid will be noted as $M_1$

Step 2

| Calcination at 600–650° C. | 4 h | 4 h |
|---|---|---|

The resulting solid will be noted as $M_2$

Step 3

| Conc. oxalic acid sol. (M) | 0.06 | 0.12 |
|---|---|---|
| Duration (in h) | 3 | 2.5 |
| Temperature (° C.) | 80 | 80 |
| Conc. of solid (wt %) | 4 | 10 |
| Mole $H^+$ $g^{-1}$ solid | 0.0015 | 0.0012 |

The resulting solid will be noted as $M_3$

Step 4

| Conc. NaCl solution (M) | 1 | 3 |
|---|---|---|
| Number of renewals | 5 × 12 h | 5 × 12 h |
| Temperature (° C.) | 95 | 95 |
| Conc. of solids (wt %) | 1.6 | 5 |

The resulting solid will be noted as $M_4$

Pillaring Procedure

Step 5

| Pillaring solution: |  |  |
|---|---|---|
| OH/Al molar ratio: | 2.4 | 2.4 |
| mmol Al $g^{-1}$ solid | 24 | 24 |
| Contact time (in h) | 4 | 4 |
| Temperature (° C.) | 80 | 80 |

The resulting solid will be noted as $M_5$, the pillaring operating step 5 is described below.

Step 5.—Pillaring Operation

The Na-exchanged mica M4 was dispersed in water (1 wt % of solid), and stirred for 24 h (avoided in continuous process). Pillaring was done according to existing procedures, as e.g. by slow addition of the pillaring solution to the mineral dispersion under stirring while the temperature was increased to 80° C. (not indispensable). The volume of the $Al_{13}$ solution (pillaring solution) was adjusted in order to supply a sufficient amount of the pillaring element (12 to 36 mmol Al per gram of mica, typically 24 mmol $g^{-1}$).

The contact between the pillaring solution and the solid was maintained for 4 hours after the end of the addition, at 80° C. (not indispensable) under continuous stirring. The solution was eliminated by centrifugation and the sample was washed until the conductivity was reduced to 0.5 $\mu S$ $cm^{-1} 1$ $g^{-1}$ (sample $M_5$). Sample $M_5$ was dried at 60° C. and calcined at the desired temperature for characterization purposes.

Two different $Al_{13}$ sources (pillaring solutions) have been used: a base (e.g. NaOH) hydrolysed Al solution (e.g. $AlCl_3$), and a commercial solution of Al-chlorhydrol (from Reheis Chem. Co., Ireland).

a) Pillaring With Base Hydrolysed Al Solution (Typical Pillaring Solution)

The pillaring solution was prepared (as in previous works [references 12–14]) by slow addition of a 0.2 M NaOH solution to a 0.2 M solution of $AlCl_3$, under stirring at 80°

C. The required volume of base was added to reach an OH/Al molar ratio of 2.4. The Al concentration in the final solution was 0.06 M. The solution was aged at room temperature for at least 24 h (not indispensable). It has been established that in solutions with this molar ratio, about 70–80% of the total aluminium ions are present as '$Al_{13}^{7+}$' oligocations [references 10, 11–14].

Notes:

OH/Al molar ratio is not limited to 2.4 as in the example.

Al concentration of the pillaring solution is not limited to 0.06 M b) Pillaring With Commercial Al-chlorhydrol (Reheis Chemical Company, Dublin).

Al-chlorhydrol (or commercial equivalents with trade name PAX and OCAL) is formed by the reaction of metal aluminium with aqueous $AlCl_3$. These solutions also contain oligomers larger than $Al_{13}^{7+}$ [reference 15]. The analysis of the starting Al-chlorhydrol (50% aluminium chlorhydrate solution) given by the supplier was as follows:

| wt % $Al_2O_3$ | wt % $Cl^-$ | Al:Cl atomic ratio | Fe (ppm) | pH of 30% wt/wt sol. |
|---|---|---|---|---|
| 23.7 | 8.25 | 1.96:1 | 46 | 4.30 |

The commercial solution was diluted to 0.1 M in Al and heated at 60° C. for 2 h immediately before use.

Notes:

Chlorhydrol may be used either undiluted or at any dilution. Dilution is however preferred Heating and ageing of the chlorhydrol solution are not indispensable.

In the following, "standard method" will refer to the complete sequence of operations described above.

For characterisation purposes, the solids were recovered at the end of the different steps described below, washed when necessary and dried (superfluous in a continuous preparation procedure).

Characterisation of Intermediates

X-ray Diffraction Data

The spacings corresponding to the (001) reflection were determined from X-ray diffraction patterns recorded with a Philips type PW 1130-90 instrument (CoKα radiation, Fe-filtered) or a Siemens D-5000 diffractometer (CuKα radiation, Ni-filtered). The scanning rate was 1° 2θ min$^{-1}$. The spacings of intermediates are given in Table 1.

Sample $M_1$ (Treated With Nitric Acid, Washed and Dried at 60° C.):

Three peaks appeared in the low angle region, one with spacing of 10.1 Å (starting phlogopite), and two new peaks at d=25 Å (absent in the starting mica) and at 11.6 Å. After calcination at 500° C., only the peak at 10.1 Å remained.

Sample $M_2$:

After calcination of $M_1$ at 600° C., only one peak remained at 10 Å.

Sample $M_3$:

Spacing analogous to that of $M_2$

Sample $M_4$:

Suitable Na-exchange was characterised by the expansion of the basal spacing to 12.2 Å at 60° C. (another peak with d=14.5 Å was observed in higher humidity conditions). Na-exchange was confirmed by the contraction of the basal spacing to 9.7 Å after heating at 500° C.

TABLE 1

| | XRD data: interplanar distances (in Å) | |
|---|---|---|
| Sample | At room temperature | At 500° C. |
| $M_i$ | 10.1 | 10.1 |
| $M_1$ | 25, 11.7–11.5, 10.1 | 10.0 |
| $M_2$ | 10.0–10.15 | — |
| $M_3$ | 10.1–10.25 | 10.05 |
| $M_4$ | 12.2, (14.5) | 9.7 |
| $M_5$ | 18.5, (14.1–13.8)* | 18.3–17.7 |

*very weak intensity

Textural Characteristics

The surface areas ($S_{BET}$) were obtained by applying the BET treatment to the nitrogen sorption isotherms measured at 77K (ASAP 2000 Sorptometer, from Micromeritics) in the domain of relative pressures of 0.05–0.25, on samples previously outgassed for 6 h at 200° C. The total pore volumes (Vo) were established from the amount of nitrogen adsorbed at a relative pressure of 0.985, and the micropore volumes (Vµ) were calculated by the 't-plot' method [reference 16].

The experimental values are given in Table 2. The Na-exchanged sample ($M_4$) showed almost no microporosity, and a small increment of the surface area and the total pore volume with respect to the starting mineral ($M_i$).

TABLE 2

Textural characteristics of samples calcined at 500° C. BET specific surface area ($S_{BET}$), total pore volume ($V_O$) and micropore volume ($V_\mu$, t-plot method).

| Sample | $S_{BET}$ ($m^2\ g^{-1}$) | $V_O$ ($cm^3\ g^{-1}$) | $V_\mu$ ($cm^3\ g^{-1}$) |
|---|---|---|---|
| $M_i$ | 2 | 0.010 | 0.000 |
| $M_4$ | 28 | 0.067 | 0.000 |

An illustration of the complete $N_2$ isotherms of $M_i$ and $M_4$ (outgassed at 200° C.) is shown in FIG. 1.

During the conditioning step, the particle size (measured with a Coulter LS130 apparatus) was almost unchanged in the medium and small size part of the distribution curve. A diminution of the size of the larger fraction was noticed, as shown in Table 3.

TABLE 3

| | Particle size analysis (0.1 µm–900 µm) | | | |
|---|---|---|---|---|
| Sample | Mode (µm) | Size (µm) 90%< | Size (µm) 50%< | Size (µm) 10%< |
| $M_i$ | 67 | 277 | 59 | 17 |
| $M_4$ | 61 | 110 | 50 | 16 |

Other Characteristics

The cation exchange capacity (CEC) of $M_4$, determined by micro-Kjeldahl analysis on an ammonium-exchanged sample, was 1.46 meq g$^{-1}$.

The $^{27}$Al MAS-NMR spectrum of the starting mica (Mi in FIG. 2) (recorded with a Bruker 400 MSL spectrometer; magnetic field of 9.4 T; pulse length of 0.6 µs; tipping angle of 10°; recycle delay of 0.1 s; spinning rate of the 4 mm diameter rotor: 12 kHz; number of scans: 3000) showed a signal at 63 ppm, characteristic of tetrahedral aluminium. After acid leaching (spectrum M1), there is a decrease of the signal at 63 ppm and a new signal appears at around 0–3 ppm, indicating that part of the tetrahedral Al has been converted to extraframework octahedral Al. The signals at 190 ppm and −60 ppm are side bands associated to the main signal at 63 ppm. After carrying out step 2 (spectrum M2), the signal at 0–3 ppm is much reduced and slightly shifted to 10 ppm. It has almost totally disappeared after the sodium exchange (spectrum M4). The spectrum of the Al-pillared mica (M5) exhibits an intense signal at about 0 ppm, typical of octahedral Al of the pillars. The two signals at about 140 and −120 ppm are side bands associated with that at 0 ppm.

Characterization of Al-pillared Micas

Sample $M_5$:

After treatment with the pillaring solution, intercalation of the $Al_{13}$ species was evidenced by the expansion of the spacing to 18.7–18.5 Å. A minor fraction of the mica was intercalated with smaller aluminium species (mainly monomeric aluminium), characterised by a diffraction peak at 14.1–13.7 Å.

Heating $M_5$ at 500° C. resulted in a limited contraction due to dehydration-dehydroxylation of the pillar precursor (Keggin-type cation) to the corresponding pillar oxide. This contraction was shown by a small shift of the 001 reflection from 18.5 Å to 18.3–17.7 Å, depending on the calcination conditions, while the minor fraction intercalated with monomeric species collapsed to 10.5 Å. These changes are summarized in Table 1.

Thermal Stability, Textural and Structural Characteristics (Al-pillared Micas)

The DTG curve (obtained with a Setaram TG-DTA 92 thermobalance in dynamic air atmosphere and heating rate of 10° C. min$^{-1}$) showed that adsorbed water is removed at 150° C. A continuous weight loss occurred between 150 and 500° C. associated with the dehydroxylation of the OH ligands of the aluminium pillars. Dehydroxylation of the mica structure occurred at 800–850° C. The total weight loss (60–1000° C.) was 22.2%.

The textural characteristics established from the nitrogen sorption isotherms are given in Table 4. The micropore volumes of the pillared micas were determined according to a method-described in [reference 17].

The specific surface areas and the micropore volumes remain nearly constant after calcination up to 600° C. and keep high values even at 700° C. A noticeable decrease of the surface area and microporous volume is observed after calcination at 800° C. At 850° C. and above, the structural identity of the pillared material is lost.

TABLE 4

Textural characteristics of pillared samples after calcination. (heating rate: 1° C. min$^{-1}$ with a plateau of 2 h at the final temperature; outgassing at 200° C. under 10$^{-4}$ Torr)

| Sample | $S_{BET}$ (m$^2$ g$^{-1}$) | $V_0$ (cm$^3$ g$^{-1}$) | $V_\mu$ (cm$^3$ g$^{-1}$) |
|---|---|---|---|
| $M_5$-RT (batch 2) | 356 | 0.220 | 0.129 |
| $M_5$-RT (batch 1) | 351 | 0.250 | 0.123 |
| $M_5$-400 (batch 2) | 339 | 0.201 | 0.114 |
| $M_5$-500 (batch 1) | 365 | 0.268 | 0.119 |
| $M_5$-600 (batch 2) | 339 | 0.201 | 0.114 |
| $M_5$-700 (batch 1) | 283 | 0.153 | 0.094 |
| $M_5$-800 (batch 1) | 145 | 0.073 | 0.036 |

The complete $N_2$ adsorption-desorption isotherms of Al-pillared phlogopite established after calcination at increasing temperatures are shown in FIG. 1 ($M_5$-500, $M_5$-700 and $M_5$-800).

The structural changes follow a similar tendency, namely, a relatively slight diminution of the basal spacing after calcination at 400–600° C. But even at 800° C., the spacing remains quite high (see Table 5).

TABLE 5

Basal spacings (in Å) of $M_5$ after calcination for 2 h at increasing temperatures (heating rate: 1° C. min$^{-1}$; plateau of 2 h at the final temperature).

| | T (° C.) | | | | | |
|---|---|---|---|---|---|---|
| | 60 | 400 | 500 | 600 | 700 | 800 | 850 |
| $d_{001}$ | 18.7 | 18.3 | 17.7 | 17.4 | 16.2 | 16.0 | 12.7 |

The limit of the thermal stability was 840° C. (from DTA curve).

The acid content of Al-pillared phlogopite $M_5$ calcined at 500° C. (determined by adsorption of ammonia at 100° C. followed by temperature-programmed desorption (TPD) of ammonia between 100 and 550° C.) was 0.29 meq g$^{-1}$.

Intercalation of $Al_{13}$ was confirmed by $^{27}$Al MAS NMR spectroscopy. The spectrum showed an increase of the signal at 63 ppm corresponding to structural Al and to Al of the pillars, both in fourfold coordination, and a new signal at 3–4 ppm characterizing Al in octahedral coordination originating from the pillars.

Figure 2:
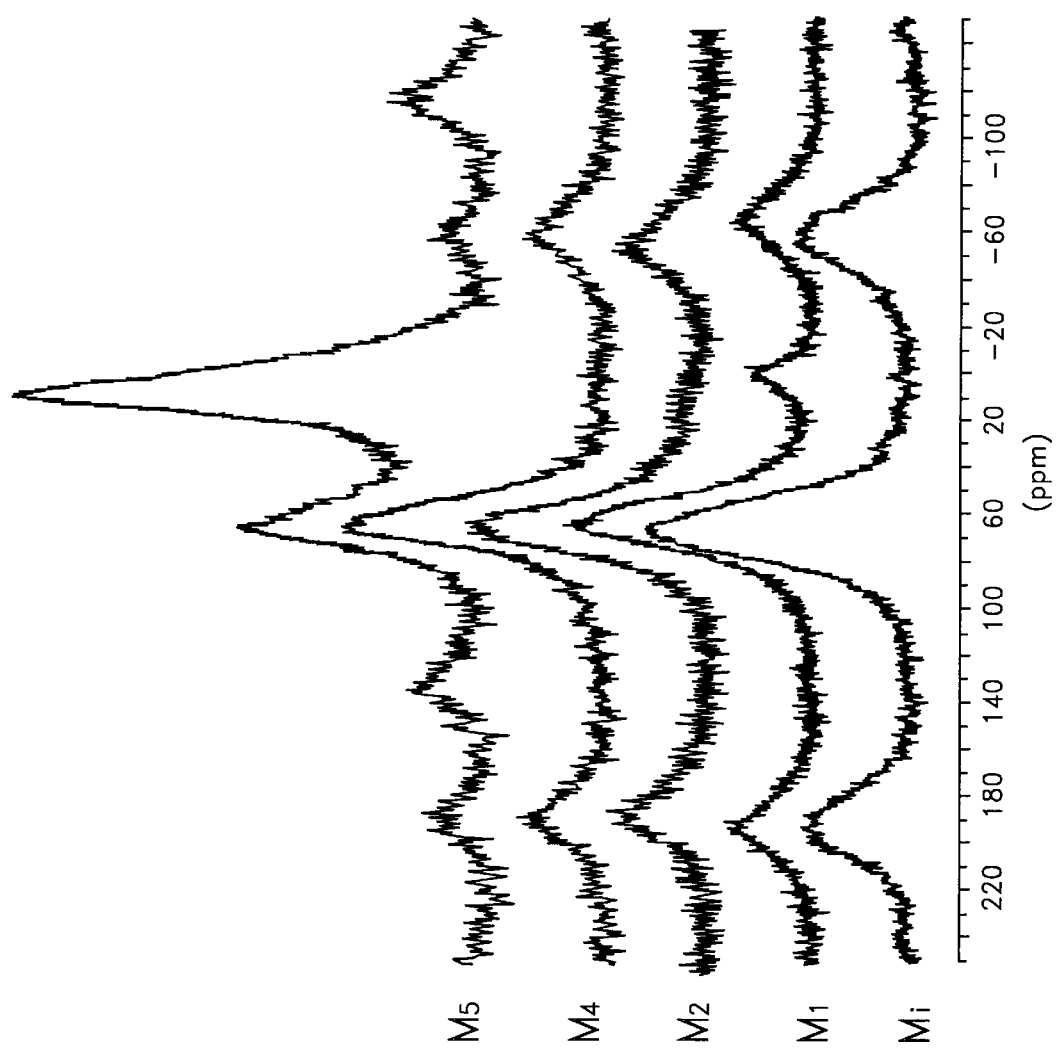
FIG. 2 represents $^{27}Al$ MAS-NMR spectra of the starting mica (Mi) and of samples collected at step 1 (M1), at step 2 (M2), at step 4 (M4) and after Al-pillaring (M5).

This is illustrated in FIG. 2 which compares the spectra obtained for the starting mica (1), after Na-exchange (2), and after pillaring (3). The signals showing up above 100 ppm and below −20 ppm are side bands.

Variation of Some Preparation Parameters

Table 6 compiles the textural characteristics, namely the specific surface areas ($S_{BET}$), the micropore volumes [method of reference 17] ($V_\mu$), and the total pore volumes (Vo) of $M_5$ solids in relation with the conditions employed at each step.

All these pillared samples calcined at 500° C. showed basal spacings between 17.4 Å to 18 Å.

TABLE 6

Textural parameters of selected samples (not typical conditions)

| Sample | step 1 | step 2 | step 3 | step 4 | step 5 | $S_{BET}$ $m^2g^{-1}$ | $V_\mu$ $cc\ g^{-1}$ | $V_o$ $cc\ g^{-1}$ |
|---|---|---|---|---|---|---|---|---|
| $M_S$-500 | 0.29 | 500 | citric | 6 × 1M | lab-12 | 228 | 0.086 | 0.147 |
| $M_S$-600 | 0.29 | 500 | citric | 6 × 1M | lab-12 | 222 | 0.073 | 0.146 |
| $M_S$-700 | 0.29 | 500 | citric | 6 × 1M | lab-12 | 218 | 0.074 | 0.137 |
| $M_S$-500 | 0.29 | 500 | ox | 5 × 1M | lab-12 | 287 | 0.083 | 0.165 |
| $M_S$-500 | 1.44 | 500 | ox' | 5 × 1M | lab-24 | 261 | 0.097 | 0.191 |
| $M_S$-700 | 1.44 | 500 | ox' | 5 × 1M | lab-24 | 237 | 0.080 | 0.181 |
| $M_S$-500 | 1.44 | 500 | ox' | 4 × 1M | lab-12 | 261 | 0.089 | 0.193 |
| $M_S$-500 | 1.44 | 500 | ox' | 4 × 3M | lab-12 | 237 | 0.079 | 0.163 |
| $M_S$-500 | 0.72 | 500 | ox" | 5 × 1M | lab-12 | 279 | 0.105 | 0.186 |
| $M_S$-500 | 0.72 | h500 | ox" | 5 × 1M | lab-12 | 234 | 0.086 | 0.155 |
| $M_S$-200 | 0.29 | 500 | ox | 5 × 1M | lab-36 | 310 | 0.115 | 0.210 |
| $M_S$-500 | 0.29 | 500 | ox | 5 × 1M | lab-36 | 264 | 0.094 | 0.193 |
| $M_S$-600 | 0.29 | 500 | ox | 5 × 1M | lab-36 | 267 | 0.083 | 0.200 |
| $M_S$-400/1 | 0.78 | 500 | ox' | 3 × 3M | Chlr-24 | 196 | 0.025 | 0.153 |

Step 1:
Column entitled "step 1" gives the molar concentration (M) of the nitric acid solution.
The concentration of solids was 3 wt % for 0.29 M nitric acid; 10 wt % for 0.72 M and 0.78 M; and 20 wt % for 1.44 M (constant mol H$^+$ g$^{-1}$ solid=0.007).
Step 2:
Column "step 2" shows the heating temperature; h meaning no drying prior to thermal treatment.
Step 3:
Column "step 3" gives a code related to the nature of the complexing solution, time and temperature used. The meaning of the code is the following: ox: 0.06 M oxalic acid, 4 h, 80° C.; ox': 0.12 M oxalic acid, 3 h, 80° C.; ox": 0.06 M oxalic acid, 3 h, 95° C.
Step 4:
This column refers to the number of ion exchange operations performed (renewals of the exchange solution); xM refers to the molarity of the NaCl solution.
Step 5:
Column "step 5" indicates the type of pillaring solution: lab: prepared by base-hydrolysis of AlCl$_3$ solution (OH/Al= 2.4); Chlr: commercial Chlorhydrol; –12 and –24 stand for the amount of Al supplied per g mineral, respectively, 12 and 24 mmol Al g$^{-1}$ clay.
Calcination in mufle oven (heating rate: 12–13° C. min$^{-1}$).
Note: Trials using at step 3 acetic and hydrochloric acid in place of oxalic or citric acid gave as well pillared micas with c.a. 18 Å spacings (samples calcined at 500° C.). At the difference with samples treated with the preferred acids, the X-ray pattern exhibited a second reflection at 14 Å (room temperature drying) which was more significant than in samples using oxalic or citric acid, but less important than when step 3 was omitted.
The intensity ratios of the 18 Å phase to the 14 Å phase in samples treated with acetic acid, hydrochloric acid, and when omitting step 3 in samples dried at room temperature were, respectively, 3.6, 3.1 and 2.0, and increased to 16, 15 and 9 respectively after calcination at 500° C., thus showing that acetic acid and hydrochloric acid may also be used at step 3.

2. Al-Pillaring of Vermiculites

Vermiculites from Palabora Company (South Africa) and Libby (Montana) deposit were treated following the "standard method" and characterised.

Starting Vermiculites

The vermiculite from Palabora Company was superfine grade and it is noted as $P_i$. The vermiculite from Libby (Montana) deposit is noted as $L_i$.

The C.E.C. determined on Ba-exchanged $P_i$ was 1.85 meq g$^{-1}$

The chemical analyses obtained by I.C.P.S. for $P_i$ and $L_i$ are given in Table 7 (in wt %):

TABLE 7

Chemical analysis data (wt %) on basis of samples calcined at 1000° C.

| | SiO$_2$ | Al$_2$O$_3$ | Fe$_2$O$_3$ | MgO | CaO | K$_2$O | F$^-$ | L.I. |
|---|---|---|---|---|---|---|---|---|
| $P_i$ | 43.3 | 9.3 | 8.6 | 24.1 | 5.1 | 4.8 | 0.9 | 11.1 |
| $L_i$ | 41.2 | 9.2 | 6.8 | 28.3 | 3.3 | 4.6 | 0.2 | 12.6 |

L.I.: weight loss on ignition at 1000° C.

Pillared vermiculites were prepared according to the sequence of treatments described for the mica. Palabora and Libby vermiculites will be distinguished by, respectively, P ($P_1$ to $P_5$) and L ($L_1$ to $L_5$). The experimental conditions employed at the various steps are indicated hereafter.

Conditioning and Pillaring Conditions

Step 1:

| | |
|---|---|
| Nitric acid conc. (M) | 0.78 for $P_i$ and 0.62 for $L_i$ |
| Duration (h) | 4 |
| Temperature (° C.) | 95 |
| Concentration of solids (wt %) | 10 |

Samples $P_1$ and $L_1$

Step 2:

| | |
|---|---|
| Calcination at 600–650° C. | 4 h |

Samples $P_2$ and $L_2$

Step 3:

| | |
|---|---|
| oxalic acid conc. (M) | 0.12 |
| Duration (h) | 1 |
| Temperature (° C.) | 80 |
| Concentration of solids (wt %) | 10 |

Samples $P_3$ and $L_3$

Step 4:

| | |
|---|---|
| NaCl solution conc. (M) | 3 |
| Number of renewals | 5 × 12 h |
| Temperature (° C.) | 95 |
| Concentration of solids (wt %) | 5 |

Samples $P_4$ and $L_4$

Step 5:

| | |
|---|---|
| Pillaring solution | OH/Al = 2.4 |
| mmol Al/g solid | 24 |
| contact time (h) | 4 |
| temperature (° C.) | 80 |

Samples $P_5$ and $L_5$

Characterization of Conditioning Intermediates ($P_i$ to $P_4$, $L_i$ to $L_4$)

X-ray Diffraction Data

The spacings of the samples dried at room temperature and calcined at 500° C. at the different steps are given in Table 8.

TABLE 8

Basal spacings (in Å) of samples dried at room temperature and calcined at 500° C.

| Sample | Room T (Å) | 500° C. (Å) |
|---|---|---|
| $P_i$ | 24.5, 14.2, 12.4, 11.8 | 25, 14, 11.5, 9.9 |
| $P_1$ | 24.7, 11.9 | 9.8 |
| $P_2$ | 9.8–10.0 | |
| $P_3$ | 9.8–10.25 | 9.9 |
| $P_4$ | 12.2–12.4 | 9.7–9.65, (12.2)* |
| $L_i$ | 25, 12.6, 12.0 | 24.9, 12, 10.15 |
| $L_1$ | 25, 12.0 | 9.8 |
| $L_2$ | 10.0 | |
| $L_3$ | 10.0–10.2 | 10.0–10.2 |
| $L_4$ | 12.2–12.4, (13.6) | 9.7–9.65, (12.2)* |

*partial rehydration

The Na-exchange ($P_4$, $L_4$) was confirmed by the spacing of 12.2 Å at room temperature (hydrated form) collapsing to 9.65–9.7Å after heating at 500° C.

Textural Characteristics

Figure 3:
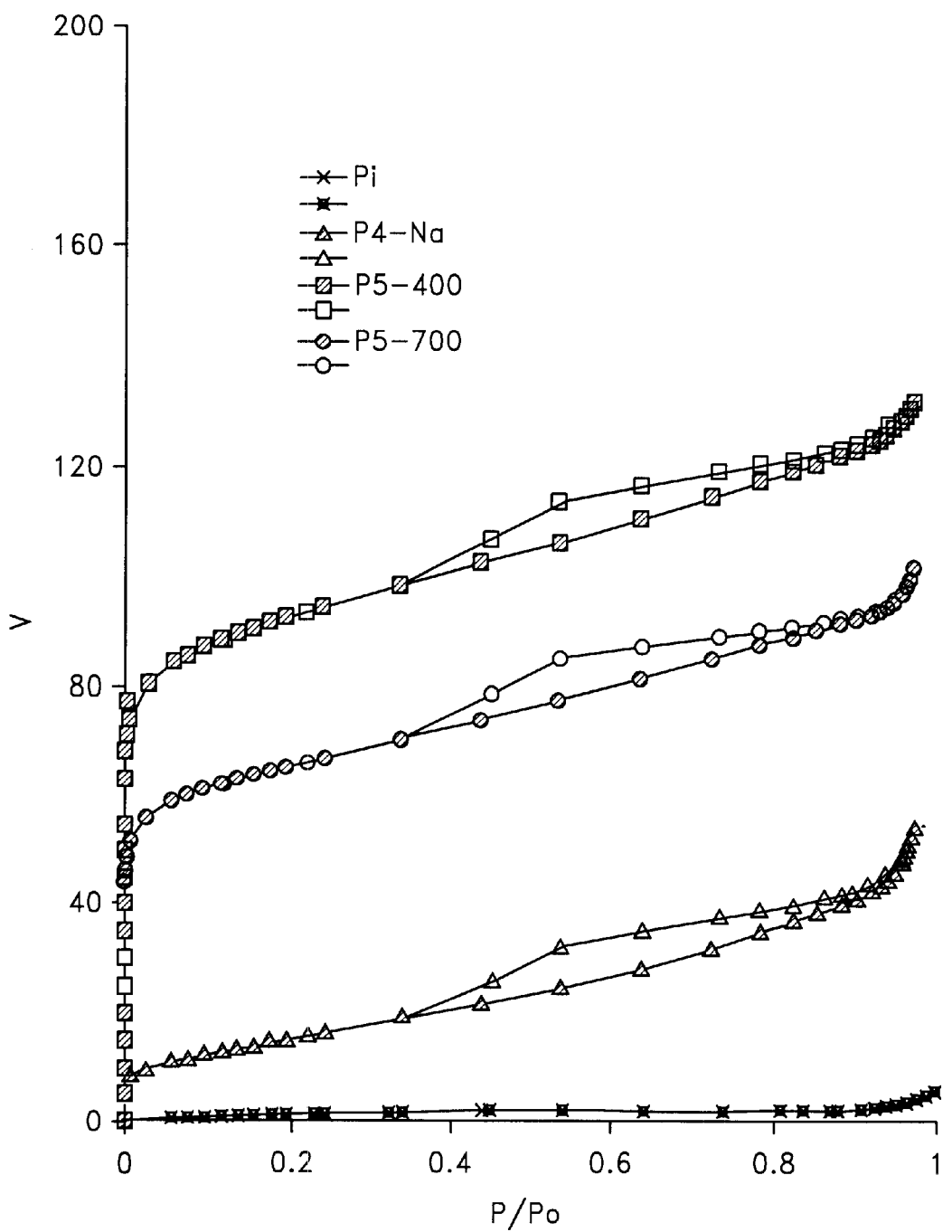
FIG. 3 represents nitrogen sorption isotherms of starting Palabora vermiculite (Pi), after sodium saturation (P4-Na), and of Al-pillared vermiculite calcined at 400° C. (P5-400) and 700° C. (P5-700). Outgassing at 200° C. for 6 h.

The Na-exchanged samples ($P_4$, $L_4$) outgassed at 200° C. for 6 h (Table 9) show no microporosity, and an increment of the surface area and of the total pore volume with respect to the starting vermiculite ($P_i$). The nitrogen sorption isotherms corresponding to $P_1$ and $P_4$ are shown in FIG. 3.

TABLE 9

Textural characteristics
Specific surface area ($S_{BET}$), total pore volume ($V_0$) and micropore volume ($V_\mu$) (t-plot method) of samples precalcined at 500° C.

| Sample | $S_{BET}$ (m² g⁻¹) | $V_0$ (cm³ g⁻¹) | $V_\mu$ (cm³ g⁻¹) |
|---|---|---|---|
| $P_i$ | 2 | 0.004 | 0.000 |
| $P_4$ | 43 | 0.074 | 0.001 |
| $L_4$ | 22 | 0.036 | 0.000 |

Particle Size Analysis

The analysis data of sample P4 are compared with those of the starting vermiculite in Table 10. As in the case of micas, a reduction of the particle size occurs during the conditioning steps.

TABLE 10

Particle size analysis (0.1 μm–900 μm)

| Sample | Size (μm) 90%< | Size (μm) 50%< | Size (μm) 10%< |
|---|---|---|---|
| $P_i$ (superfine) | 819 | 515 | 22 |
| $L_i$ | 684 | 290 | 74 |
| $P_4$ | 252 | 102 | 32 |

Other Characteristics

The CEC (cation exchange capacity) prior to pillaring ($P_4$) was 1.32 meq g⁻¹ (micro-Kjeldahl method on ammonium-exchanged form).

Note: The starting vermiculites ($P_i$, $L_i$) may be directly converted in any desired homoionic form without proceeding to steps 1 to 3. However, pillaring cannot be achieved without these steps.

Characterization of Al-pillared Vermiculites

Textural and Structural Characteristics

The textural results derived from the nitrogen sorption isotherms of sample P5 (uncalcined and previously calcined at different temperatures with heating rate of 1° C. min⁻¹) are given in Table 11. Prior to the sorption measurements, the samples were outgassed at 200° C. for 6 h.

TABLE 11

Textural characteristics.
BET specific surface area ($S_{BET}$), total pore volume ($V_0$) and micropore volume ($V_\mu$) of samples calcined at increasing temperatures

| Sample | $S_{BET}$ (m² g⁻¹) | $V_0$ (cm³ g⁻¹) | $V_\mu$* (cm³ g⁻¹) |
|---|---|---|---|
| P5-200 (Na) | 296 | 0.185 | 0.098 |
| P5-400 (Na) | 307 | 0.192 | 0.109 |
| P5-500 (Na) | 322 | 0.215 | 0.120 |
| P5-600 (Na) | 241 | 0.166 | 0.071 |
| P5-700 (Na) | 216 | 0.144 | 0.068 |
| P5-400 (Ca) | 291 | 0.197 | 0.112 |
| P5-500 (Ca) | 318 | 0.211 | 0.119 |
| P5-600 (Ca) | 326 | 0.215 | 0.123 |
| P5-700 (Ca) | 226 | 0.159 | 0.082 |
| P5-800 (Ca) | 184 | 0.138 | 0.062 |
| L5-400 (Na) | 241 | 0.158 | 0.083 |
| L5-600 (Na) | 212 | 0.142 | 0.071 |

*Method of. [reference 17]

The textural characteristics obtained on Palabora vermiculite, exchanged, at step 4, with a calcium salt instead of a sodium salt, both homoionic forms being pillared as indicated above, are compared in Table 11. The use of a Ca salt at the step 4 improves the characteristics of the pillared material at similar calcination temperatures.

The complete nitrogen adsorption-desorption isotherms of P5 calcined at 400° C. and 700° C. are shown as example in FIG. 3

As seen in Table 12, after treatment with the pillaring solution, the intercalation of the $Al_{13}$ is confirmed by the expansion of the interlayer distance to 18.7–18.2 Å. A minor fraction of the vermiculite was intercalated with smaller aluminium species (mainly monomeric aluminium) with spacings of 14.1–13.7 Å. At 400° C., the spacing was somewhat reduced (18.4 Å) and the minority fraction intercalated with monomeric species collapsed to 10.5 Å. No significant difference was noticed according to the cation species exchanged at step 4.

Figure 4:
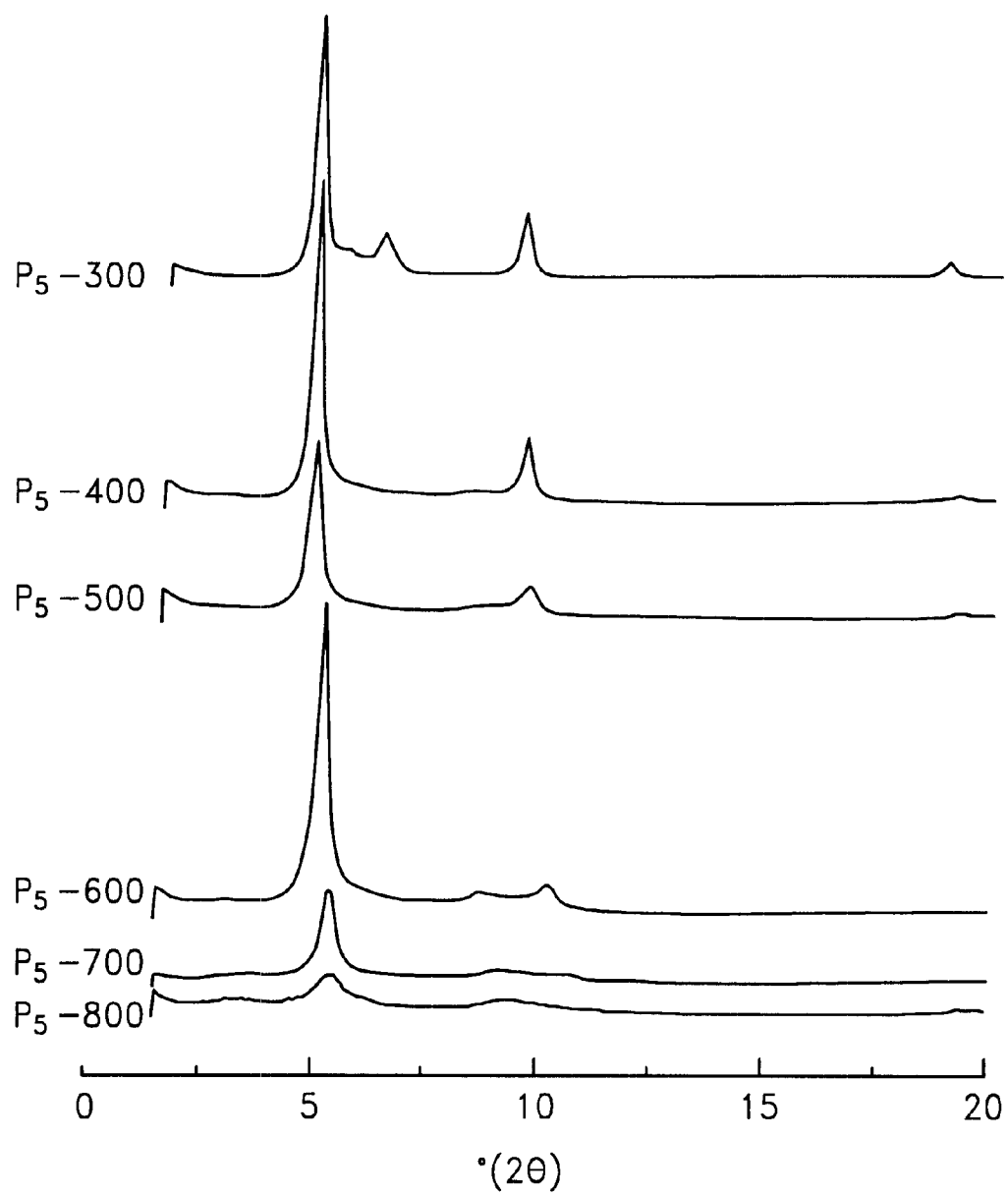
FIG. 4 represents X-ray diffraction patterns of Al-pillared Palabora vermiculite (P5) after heating at different temperatures.

FIG. 4 shows the XRD diffraction patterns of the Al-intercalated Palabora vermiculite, after drying at 60° C. and subsequent calcination at increasing temperatures (in the same conditions as above).

TABLE 12

Basal spacing d001 (Å) of pillared vermiculites
(Samples calcined at heating rate of 1° C./min;
plateau maintained for 2 h).

| T (° C.) | 60 | 400 | 500 | 600 | 700 | 800 |
|---|---|---|---|---|---|---|
| P5 (Na) | 18.7 | 18.4 | 18.2–17.7 | 17.2 | 16.4 | 16.3 |
| P5 (Ca) | 18.7 | 18.2 | 17.7 | 17.2 | 16.7 | 16.0 |
| L5 (Na) | 18.7 | 18.2 | 17.8 | 17.5 | 16.6 | — |

3. Al-Pillaring of Precalcined Vermiculites

Starting Vermiculite

Exfoliation of vermiculite is done by feeding crude vermiculite at controlled rate in a vertical furnace heated at 800–1000° C. The residence time is of the order of a few seconds, during which the hydration water around the charge balancing cation ($Mg^{2+}$) is instantaneously vaporized. Due to high local steam pressure in the interlayers, flash expansion of the vermiculite platelets occurs, with a ten- to twenty-fold expansion of the platelets, resulting in low density multilayer particles. These exfoliated vermiculites are employed e.g. for their thermal insulating properties. Separation of the fines is done e.g. by cyclonisation. These fines are not recycled (wastes).

The fine fraction of Palabora vermiculite with mean particle size of 50 μm recovered after the cyclonisation step will be referred to hereafter as "precalcined vermiculite" (previously named 'wastes'). Small amounts of calcite and possibly biotite were identified by X-ray diffraction. The experiments were done on the as received sample, without grinding and fractionation treatments.

The cation exchange capacity (CEC) of the starting sample was 0.48 meq $g^{-1}$, namely, about three times less than normal value found for crude trioctahedral vermiculites (example II). This low value is probably related to the previous flash treatment at 800° C. The starting vermiculite will be noted as $V_i$.

Conditioning of the Precalcined Vermiculite

Conditioning consisted of submitting the starting vermiculite to a similar sequence of treatments (standard method) as that for micas and crude (uncalcined) vermiculites. The conditions were as follows Step 1:

The starting vermiculite was treated with a 0.23 M solution of nitric acid at 95° C. for 4 h and under continuous stirring, using 25 ml of the acid solution per gram of vermiculite. The acid-leached solid was thoroughly washed and dried at 60° C. (Sample $V_1$ hereinafter).

Step 2:

Solid $V_1$ was calcined at 600° C. for 4 h under static air (sample $V_2$).

Step 3:

Sample $V_2$ was leached for 4 h at 80° C. under continuous stirring with a 0.5 M citric acid solution (pH=2.1) using 40 ml $g^{-1}$ of solid. The solid was washed free from excess acid and salts, and dried at 60° C. (sample $V_3$).

Step 4:

Solid $V_3$ was treated 5 times (for 12 h each) with a 1 M sodium chloride solution (50 ml $g^{-1}$ of solid). The exchange operation was preferably carried out at 95° C. under continuous stirring. The solid recovered was washed and dried at 60° C. (sample $V_4$).

At the end of this four steps treatment, the Na-exchanged vermiculite was ready for the pillaring operation. Note that at step 4, the Na-vermiculite may be converted via any usual exchange method to any desired cationic form.

Al-pillaring of Precalcined Vermiculite

The Na-exchanged vermiculite obtained at the end of step 4 (sample $V_4$) was dispersed in water (0.5 wt % of solid) and the suspension was stirred for 24 h (unnecessary in a continuous procedure). The Al-pillaring solution (base hydrolyzed $AlCl_3$, with OH/Al molar ratio of 2.4) was slowly added under stirring to the vermiculite dispersion, adding a sufficient volume to supply 12 mmol Al $g^{-1}$ vermiculite.

After addition of the pillaring solution, the final suspension was aged for 4 h at 80° C. under stirring. The suspension was centrifuged and the solid was washed and dried at 60° C. (sample noted $V_5$). The dried sample was then calcined for two hours at 500 and 700° C., using a heating rate of 13° C./min.

Characterization of Intermediates (Samples $V_1$ to $V_4$)

The solids obtained at each separate step were characterised with the same techniques and methods as for the preceding examples. As mentioned earlier (in examples I and II), in the continuous preparation process, namely, from the starting vermiculite ($V_i$) to its Al-pillared form ($V_5$), intermediate dryings are omitted.

The main observations concerning the solids obtained at the end of steps 1 to 4 are summarised hereafter. The characterisation of the Al-pillared vermiculite ($V_5$) will be treated separately.

X-ray Diffraction

The basal spacings of samples (previously calcined for 2 h at 500° C.) obtained at the end of steps 1 to 4 are given in Table 13.

TABLE 13

| Basal spacings (in Å) at 500° C. | |
|---|---|
| $V_i$ | 10.15 |
| $V_1$ | 10.1 |
| $V_2$ | 10.1 (600° C.) |
| $V_3$ | 10.15 |
| $V_4$ | 9.7 (12.1) |

The diffraction pattern of the starting vermiculite ($V_i$) exhibited reflections of hydrated vermiculite (peak at 14.5 Å), biotite (10.1 Å) and interstratified, R=1, biotite-vermiculite with interplanar distances of 25.2 and 12.2 Å.

After acid leaching and calcination at 500° C. ($V_1$-500), the interstratified phase disappeared and a single reflection at 10.1 Å with a much increased intensity was noticed.

The X-ray patterns of the samples $V_2$ (thermal treatment) and $V_3$ (citric acid leaching) did not exhibit significant modification with respect to that of calcined $V_1$.

A small but qualitatively important decrease of the basal spacing was noticed for the Na-exchanged vermiculite ($V_4$-500), with a contraction of 0.3–0.4 Å, indicative of total exchange. Partially Na-exchanged samples exhibited, after calcination at 500° C., peaks corresponding to interplanar distances of 10.1 and 9.9 Å.

As it will be illustrated below, well pillared vermiculites were only obtained from thoroughly exchanged Na-vermiculite, as for the preceding examples.

Cation Exchange Capacity

After treatment with nitric acid (sample $V_1$) the cation exchange capacity increased from 0.48 ($V_i$) to 1.49–1.50 meq g$^{-1}$. Treating vermiculite in step 1 with nitric acid (0.23 M at 95° C. for 4 h) or citric acid (0.5 M at 80° C. for 4 h) gave solids with identical CECs.

After calcination at 600° C. (sample $V_2$), the CEC decreased from 1.50 to 1.11 meq g$^{-1}$ (a loss of about 26%).

Removal of the interlayer species upon treatment with citric acid (sample $V_3$) resulted in an increase of the CEC, from 1.11 to 1.23 meq g$^{-1}$. The initial value of 1.50 meq g$^{-1}$ was not restored, which indicates a reduction of the overall negative charge.

Textural Properties

Figure 5:
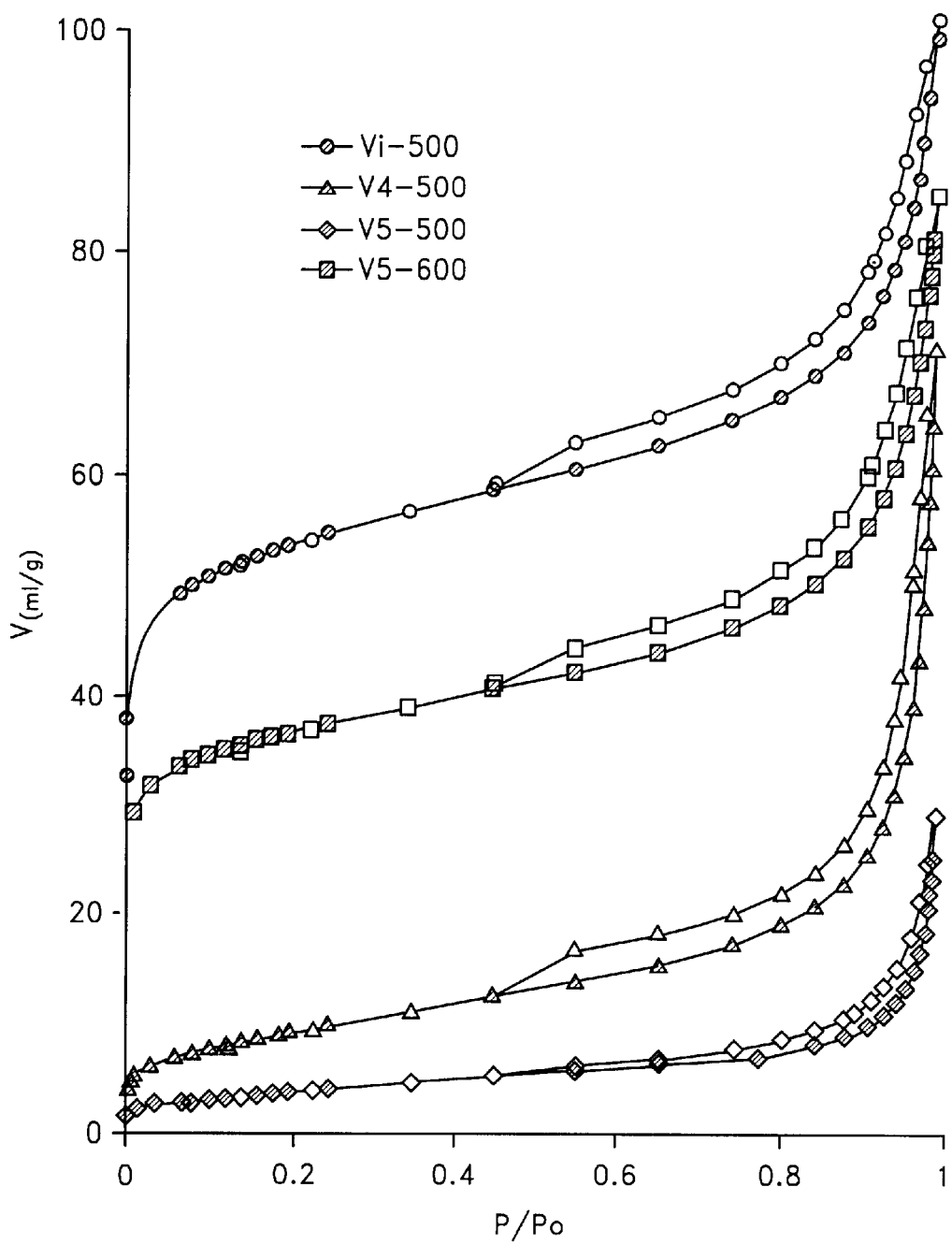
FIG. 5 represents nitrogen sorption isotherms of the starting pre-calcined vermiculite (Vi-500), after sodium exchange (V4-500), and of Al-pillared vermiculite calcined at 500° C. (V5-500) and 600° C. (V5-600).

The nitrogen adsorption-desorption isotherms at 77K of the starting ($V_i$-500) and Na-exchanged vermiculites ($V_4$-500), shown in FIG. 5, correspond to type IV of the IUPAC classification, characteristic of mesoporous solids, with a H3-type hysteresis loop, generally encountered for (layered) lamellar minerals [reference 18].

The textural characteristics of samples $V_i$ to $V_4$ are indicated in Table 14.

TABLE 14

Textural parameters of selected samples

| Sample | $S_{BET}$ (m$^2$ g$^{-1}$) | $V_\mu$ (cm$^3$ g$^{-1}$) | $V_0$ (cm$^3$ g$^{-1}$) |
|---|---|---|---|
| $V_i$ | 11 | 0.000 | 0.031 |
| $V_1$ | 68 | 0.008 | 0.097 |
| $V_2$ | 20 | 0.001 | 0.057 |
| $V_2$-Na | 17 | 0.001 | 0.050 |
| $V_4$ | 30 | 0.001 | 0.086 |
| $V_5$-500 | 153 | 0.056* | 0.121 |
| $V_5$-500 | 192 | 0.066* | 0.177 |
| $V_5$-500 | 179 | 0.065* | 0.150 |
| $V_5$-700 | 121 | 0.041* | 0.118 |

*method of [reference 17]

As shown in Table 14, the treatment with nitric acid enhances the external surface area, from 11 m$^2$ g$^{-1}$ (untreated vermiculite, $V_i$) to 68 m$^2$ g$^{-1}$ ($V_1$) mainly attributable to the increase of the macropore volume. Micropores are almost absent.

The thermal treatment (sample $V_2$) provoked a diminution of the specific surface area, from 68 to 20 m$^2$ g$^{-1}$.

The nitrogen sorption isotherms established on samples $V_2$ (not shown) and $V_4$ did not exhibit marked differences. The specific surface area of the vermiculite subsequently leached with citric acid (step 3) and Na-exchanged (step 4) was 30 m$^2$ g$^{-1}$ (V4 in Table 14), thus only slightly higher.

Characterization of Al-pillared Precalcined Vermiculites

X-ray Diffraction Analysis

The pillaring step is of course the one which leads to the obtention of pillared vermiculite and, according to whether a 18 Å phase (at room temperature) is achieved or not, it constitutes somehow an 'enlightener' on whether the intermediate steps were or were not properly conducted.

Figure 6:
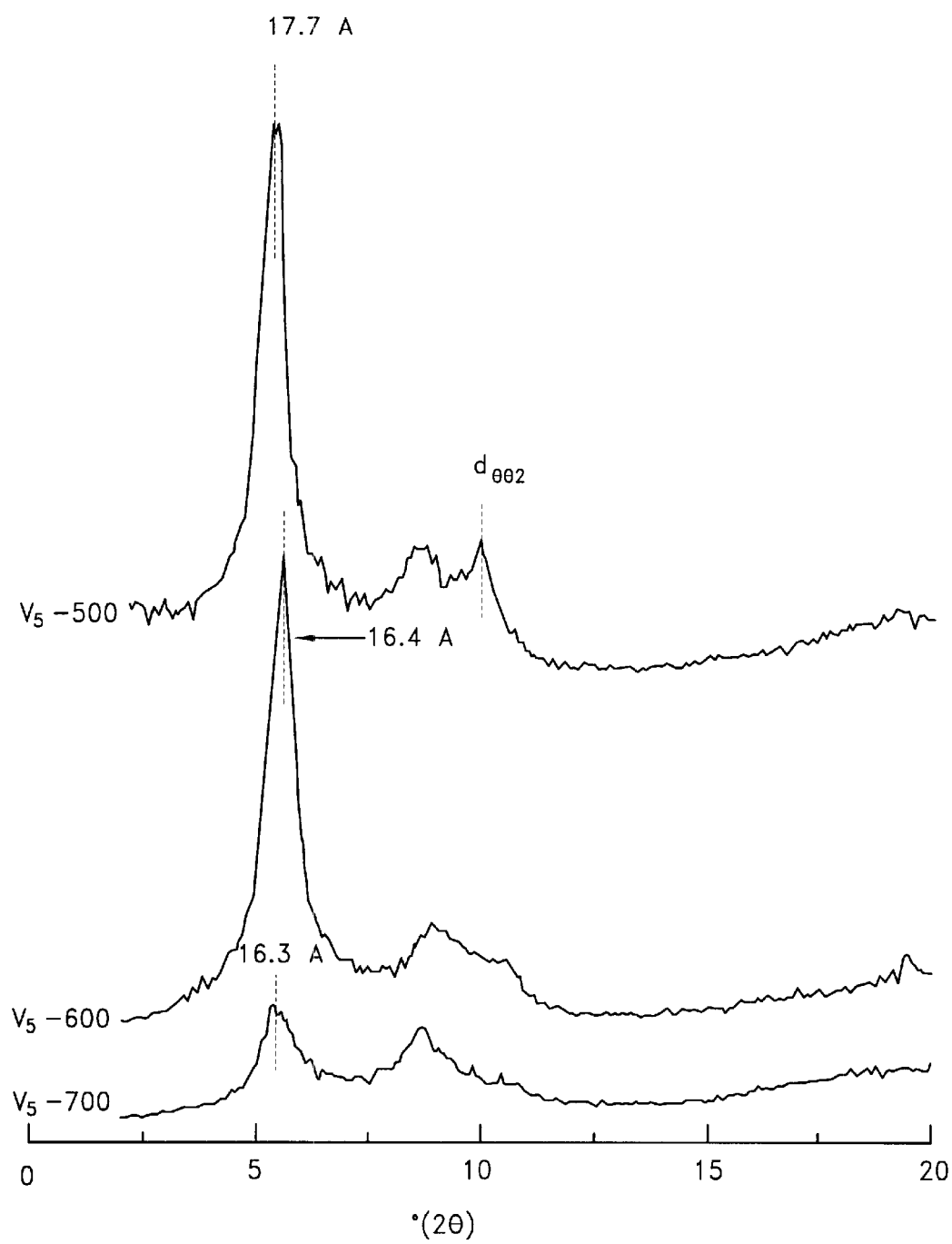
FIG. 6 represents X-ray diffraction pattern of Al-pillared precalcined vermiculite after heating at 500° C. (V5-500), 600° C. (V5-600), and 700° C. (V5-700).

FIG. 6 shows the XRD patterns of $V_5$ after calcination between 500° C. and 700° C. The basal spacings of selected samples after calcination are given in Table 15

TABLE 15

Basal spacings (in Å)

| Sample | Spacing (Å) |
|---|---|
| $V_5$'-500 (without step 3) | 17.6–17.7 |
| $V_5$-500 | 17.6–17.7 |
| $V_5$-600 | 16.4 |
| $V_5$-700 | 16.3 |

Al-pillared vermiculite exhibited a basal spacing of 18.6 Å for sample dried at room temperature, and 17.6 Å after calcination at 500° C. (Table 15). Similar spacings were found for Al-pillared micas and Al-pillared crude vermiculite.

Pillared and Al-exchanged phases can be easily distinguished on the XRD patterns. In order to evaluate the quality of the pillared materials, the ratio between the peak height of the 001 reflection of the pillared phase (ca. 17.6 Å at 500° C.) and that of the peak corresponding to the Al-exchanged vermiculite (peak at 10.5 Å at 500° C.), in short as $I_{18}/I_{10}$, is used, after background subtraction. For instance, there was a substantial increase of the peak intensity ratio ($I_{18}/I_{10}$) when the material obtained at the end of step 2 was treated with citric acid ($I_{18}/I_{10}$=7–11) compared with a sample which was not treated ($I_{18}/I_{10}$=3.1).

Thermal Stability

Pillared vermiculite calcined at 500° C. had a spacing of 17.6–17.5 Å (Table 15) which decreased to 16.4 and 16.3 Å after calcination at 600 and 700° C. respectively. The decreasing interplanar distances are similar to those observed for pillared micas.

Thermogravimetry (TGA, DTG)

The pillaring of vermiculite was confirmed by TGA data. The Al-pillared $V_5$ sample showed between 60 and 300° C., a weight loss about twice as much as for $V_4$ (Na-vermiculite). The further loss of the OH ligands of the pillars was indicated by a DTG minimum at 515° C. The structural dehydroxylation of the vermiculite occurred at 835° C. The total weight loss between 60 and 1050° C. of the Al-pillared vermiculite amounted to 16.42%, compared with 7.1 and 9.46% for, respectively, $V_i$ and $V_4$.

Textural Characteristics $N_2$ adsorption-desorption isotherms were established on pillared samples before and after calcination at 500° C. As in the case of pillared smectites (PILCs) and pillared micas (PILMs), intercalation of Al pillars between the layers is accompanied by the development of microporosity.

As seen in Table 14, the BET surface area of samples calcined at 500° C. increased from 30 m$^2$ g$_{-1}$ before pillaring (sample $V_4$) to 179–192 m$^2$ g$^{-1}$for a sample which was previously treated with citric acid ($V_5$-500), or to 153 m$^2$ g$^{-1}$ when the citric acid leaching (step 3) was omitted ($V_5$'-500). This increase of the surface area is directly related to the development of microporosity.

Residual CEC and Acid Content

The residual CEC ($V_5$-500) obtained for a pillared vermiculite was 0.27 meq g$^{-1}$. A value of 0.29 meq g$^{-1}$ was obtained for Al-pillared micas.

The acid content (temperature-programmed desorption of ammonia between 100 and 550° C.) gave an average value of 0.20 mmol g$^{-1}$.

MAS-NMR Spectroscopy

The $^{27}Al$ MAS-NMR spectrum of $V_4$ showed only one signal at 63 ppm corresponding to structural tetrahedral aluminium (aluminium in the tetrahedral layers). The Al-pillared sample (V5-500) exhibited two signals at 3–5 ppm, typical for octahedral Al, and at 63 ppm, characteristic of tetrahedral Al. The signal near 5 ppm corresponds to $Al^{VI}$ (octahedral Al) of the pillars and the one at 63 ppm is the superimposition of the signal of $Al^{IV}$ (tetrahedral Al) of the pillars and Al in the tetrahedral layers of vermiculite.

Alternative Conditioning Treatments Investigated

In order to have a better insight into the role of each one of the different steps of the standard method, several alternatives have been examined. To check the effect of those variables on pillaring, XRD is the most adequate technique because it permits to identify the phases in presence and give an evaluation of their relative proportions.

Successful pillaring is evidenced by the absence of unpillared fraction (X-ray diffraction peak at 10.1 Å after calcination of the sample at 500° C.) after the pillaring treatment. Intercalation of All 3-type species should be favoured with respect to exchange with monomeric aluminium. The $I_{18}/I_{10}$ ratio, as defined above, ranged between 0.5, for very poorly pillared vermiculites, and 7 and higher for well pillared materials in the case of precalcined vermiculite.

Some results of additional trials investigated (summarized in Table 16) are briefly described hereafter and commented altogether. Step 3 (citric acid treatment) when not specifically targeted has been omitted because it was not indispensable to verify suitable pillaring of the material. In doing so, a more rapid information on the influence of the modified parameters can be obtained. However, better pillared materials are obtained when carrying out step 3.

TABLE 16

Main alternatives investigated.

| Trial | Step 1 | Step 2 | Step 3 | Step 4 |
|---|---|---|---|---|
| n1 | $HNO_3$ 0.17 M | | //////// | |
| | $HNO_3$ 0.25 M | | //////// | |
| | $HNO_3$ 0.46 M | | //////// | |
| n2 | citric | | //////// | |
| n3 | HCl | | //////// | |
| n4 | //////////// | //////// | | |
| n5 | $HNO_3$ | $H_2O$ | ------------ | |
| n6 | $HNO_3$ | //////// | //////// | |
| n7 | $HNO_3$ | | //////// | |
| n8 | $HNO_3$ | | | //////// |
| | $HNO_3$ | | | $NH_4^+$ |

//////// means step not performed

Trials Related With Step 1. Effect of Acid Concentration
Run 1.

In distinct experiments, acid treatment in step 1 has been performed with, respectively, 0.17 [0.006 mole $H^+$ $g^{-1}$], 0.25 [0.009 mole $H^+$ $g^{-1}$], and 0.46 [0.016 mole $H^+$ $g^{-1}$] M nitric acid solutions, keeping constant the solid concentration (thus changing the mol $H^+$ $g^{-1}$ solid ratio), the leaching temperature and duration of the treatment being as in the "standard" procedure, and steps 2, 4, and 5 being subsequently carried out according to the standard procedure.

Pillaring was better achieved when vermiculite was treated with 0.009 mole nitric acid per gram solid. Using either higher or lower acid concentration resulted in poorer pillared materials. The best results were obtained when vermiculite was treated with a quantity of acid of about five to six times the CEC of the vermiculite; higher acid concentrations provoked irreversible structural damage, resulting in nonpillarable materials.

Influence of Type of Acid (Runs 2 and 3)
Run 2.

Substituting citric acid for nitric acid in step 1, in other words carrying out step 3 instead of step 1, followed by steps 2, 4 and 5, resulted in very poorly pillared material ($I_{18}/I_{10}$ ratio=0.6), suggesting that steps 2 to 5 did not operate as in the "standard" procedure.

Run 3.

Substitution of hydrochloric acid or sulfuric acid for nitric acid with similar concentration (steps 2, 4 and 5 being carried out as in the "standard" procedure) provided a pillared material in the case of vermiculite ($I_{18}/I_{10}$=6.0). For the mica, a very small fraction was pillared.

Run 4.

Experiments in which vermiculite was directly leached with citric acid followed (after washing the solid) by Na-exchange (step 4) and Al-pillaring (step 5), thus omitting steps 1 and 2 led to partial pillaring, in spite of the fact that the CEC of the Na-exchanged material obtained at step 4 was 1.49 meq $g^{-1}$ (1.50 meq $g^{-1}$ when treated with nitric acid). The $I_{18}/I_{10}$ ratio was 1.2 (1.1 in a duplicate trial). This result indicates that freeing the exchange positions of the starting vermiculite and converting it to a homoionic form are not sufficient to ensure adequate pillaring (adequate pillaring meaning that a predominant fraction of the sample is pillared).

Run 6.

Carrying out steps 1, 4 and 5 following the standard conditions (steps 2 and 3 omitted) resulted in the nearly total absence of pillaring. The $I_{18}/I_{10}$ peak ratio was only 0.46. This confirms that step 2 is indispensable to the obtention of a well pillared vermiculite.

Trials Related to Step 3 (Complexing Agent)
Run 7.

Pillared vermiculite with acceptable characteristics (spacing, surface area and micropore volume) could be obtained when the citric acid treatment was suppressed. However, carrying out this treatment resulted in a significant improvement of the characteristics of the pillared material. Using oxalic acid had a similar beneficial effect, whereas no improvement was noticed when using nitric acid instead of citric or oxalic acid in step 3. Other complexing agents (f.i. acetylacetone) were less efficient or needed longer contact times than complexing acids.

Trials Related to Step 4 (Na-exchange)
Run 8.

Attempts to suppress step 4 (sodium exchange) or to pillar ammonium-exchanged vermiculite were unsuccessful; no pillaring at all was observed. However, using calcium instead of sodium provided well pillared materials with slightly higher micropore volumes and improved resistance of the specific surface area to thermal treatment (compare P5-600 (Na) and P5-600 (Ca) of Table 11). Exchange with hydrated cations is thus of crucial importance to the obtention of well pillared vermiculites (as well as for micas) and, in particular, the degree of completion of the exchange. Indeed, a clear relation exists between the degree of exchange and the fraction of pillared vermiculite.

APPLICATION AREAS OF PILLARED MICAS AND VERMICULITES

Pillared micas and vermiculites may be used as catalysts, as such and/or in adjunction with other catalytic components, for the following reactions: cracking-hydrocracking, isomerisation-hydroisomerisation, dewaxing, alkylation and dealkylation, disproportionation-transalkylation, upgrading of light cycle oils, oligomerisation of olefins, dehydration of alcohols, hydration of olefins, ether formation, hydroxylation of phenols and derivatives, condensation reactions, methanol to hydrocarbons, hydroformylation, synthesis of glycols, CO hydrogenation, Fischer Tropsch, synthesis gas, HDS, HDN, HDM, NO reduction, deep oxidation, photocatalysis.

Pillared micas and vermiculites may find application as adsorbents; in gas separation, as scavenger for heavy metals (treatment of waste waters); $SO_2$, $NO_x$ abatement; in cation-selective composite membranes, as solid electrolytes; host material for (conducting) polymers; as host material for dispersed nitrides, oxynitrides, carbides, perovskites; modified electrodes.

In particular, the pillared micas and vermiculites obtained according to the present invention may be used in any combination with other catalytic systems as, f.i: zeolites, oxides and mixed oxides. They may also be used as a support to metals, metal oxides and metal compounds.

Chemical treatment(s) aiming to modify the surface properties of the pillared micas and vermiculites, such as treating with, e.g. phosphorus- and sulphur-containing compounds, are within the scope of this invention.

Catalytic Examples
Hydroconversion of Paraffins

Hydroisomerization of octane was conducted in the vapour phase on Pt-impregnated samples (1 wt % Pt) of Al-pillared vermiculites and micas and on a commercial zeolite Beta (ZB25 from P.Q. Zeolites) as a reference. Impregnation and activation were similar to those reported in [reference 19].

Figure 7A:
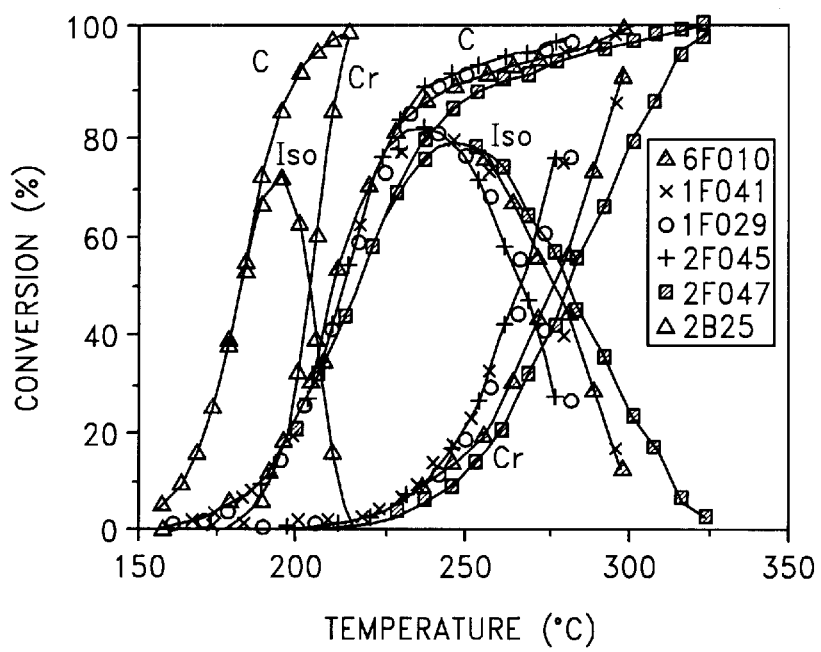
FIG. 7A represents hydroconversion of octane on Al-pillared micas: top curves: variation of total conversion (C), of the yields of C8 isomers (Iso) and of the cracked products (Cr) versus reaction temperature.
Figure 7B:
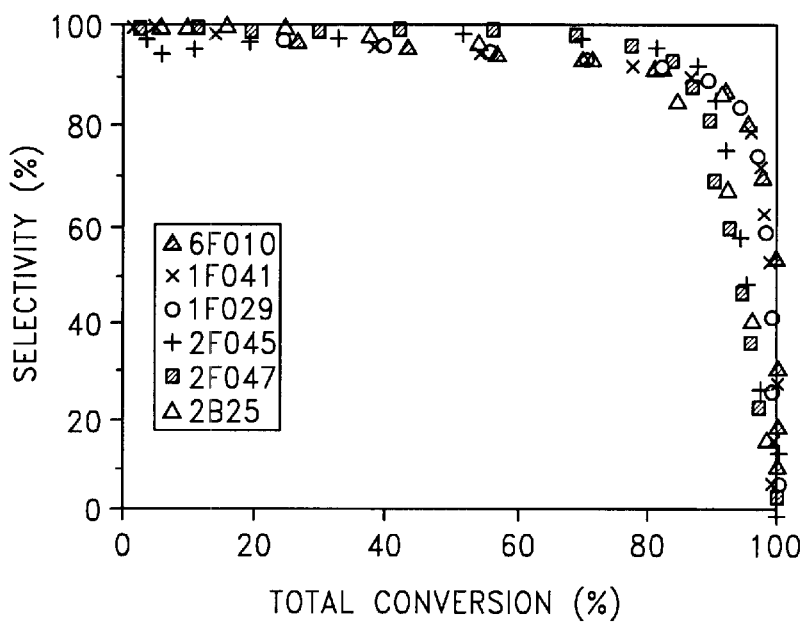
FIG. 7B represents variation of the selectivity of C8 isomers vs. octane conversion. Sample ZB25: reference zeolite beta.
Figure 8A:
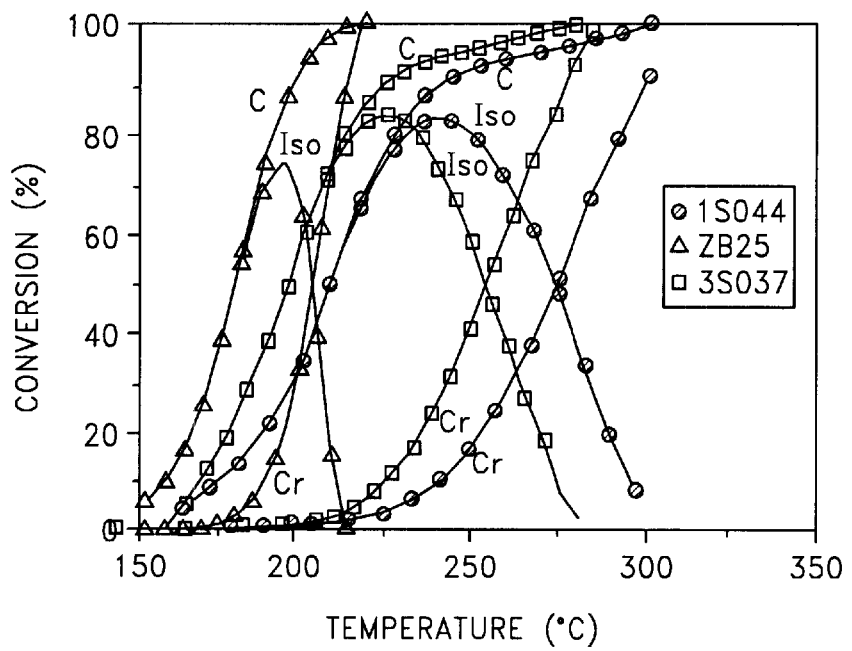
FIG. 8A represents hydroconversion of octane on Al-pillared vermiculites: top curves: variation of total conversion (C), of the yields of C8 isomers (Iso) and of the cracked products (Cr) versus reaction temperature.
Figure 8B:
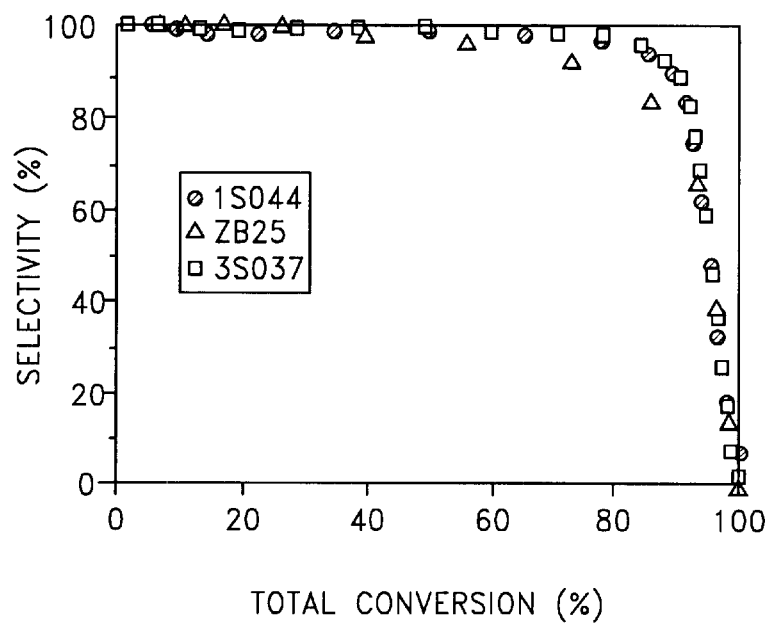
FIG. 8B represents the variation of the selectivity to C8 isomers vs. octane conversion. Sample ZB25: reference zeolite beta.

Total flow of octane-/hydrogen mixture was 10 ml min-1, WHSV: 0.92 h-1, H2/C8 15.6. Reaction was made in temperature-programmed mode (0.2° C. min-1) between 150 and 400° C. On-line analysis of the reaction products was done in a gaschromatograph equipped with flame ionisation detector and CPSil-5 capillary column. The results obtained over the zeolite beta (ZB25) and different samples of pillared micas (symbolized by F) and vermiculites (S) are shown in FIGS. 7 and 8, where the variation of total conversion, of the yields of isomers and of the cracked products are plotted against reaction temperature. Higher yields of C8 isomers are produced over the pillared micas and vermiculites compared with the reference catalyst, with, at maximum isomerisation conversion, yields of 80% for the pillared micas and vermiculites compared with 70% for the H-Beta zeolite, and selectivities to C8 isomers between 89.6 and 92.4% vs 86.2 for the zeolite.

Figure 9:
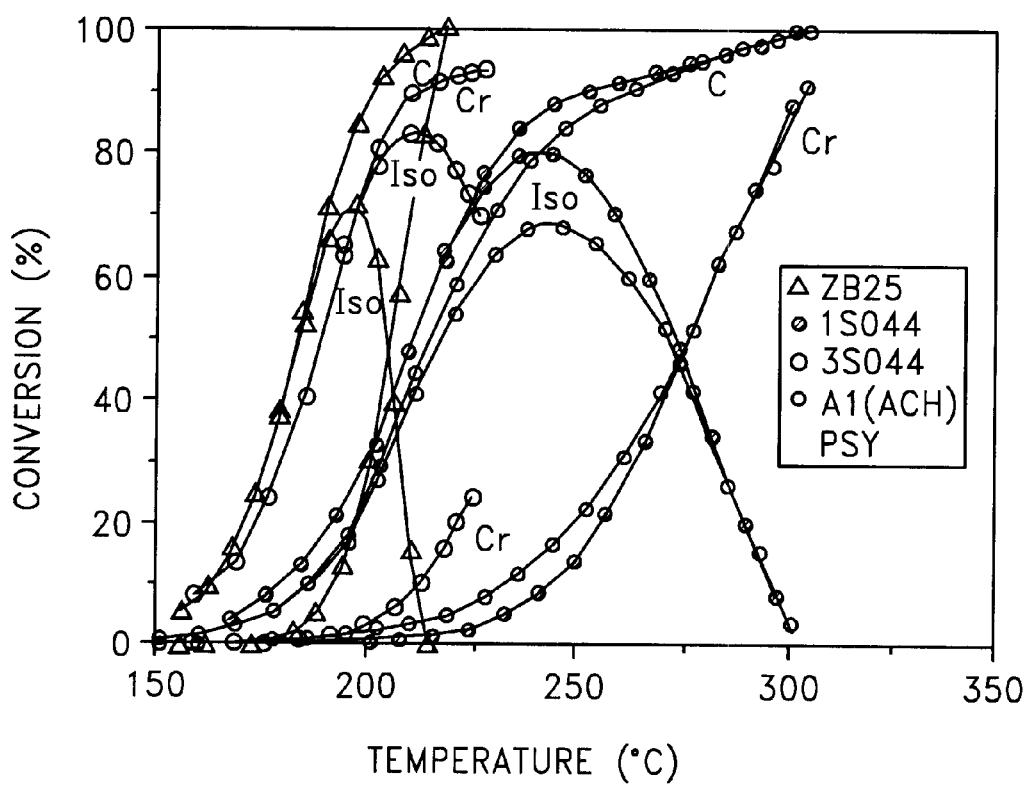
FIG. 9 represents hydroconversion of octane on Al-pillared vermiculite (1S044), on modified Al-pillared vermiculite (3S044*), Al-pillared saponite (Al(ACH)PSY), and reference H-Beta zeolite (ZB25)

For sake of comparison, results obtained at maximum isomerisation conversion on US-Y zeolites (commercial samples CBV400 to CBV780, from PQ Zeolite), H-Beta (ZB25 and ZB75 from PQ Zeolite), Al-pillared saponite (Al(ACH)PSY, a pilor scale prepared sample with Al-chlbrhydrol), and on Al-pillared micas (samples F) and Al-pillared vermiculites (samples S), all loaded with 1 w t% Pt and tested in similar conditions are compiled in Table 17. Sample 3S044 in this table is an Al-pillared vermiculite that was treated with diluted hydrochloric acid after being calcined at 500° C. (referred to as stabilized pillared vermiculite), together with those obtained on ZB25 (H-beta zeolite), Al pillared saponite (Al(ACH)PSY) and non stabilized Al-pillared vermiculite (IS044). The corresponding curves are shown in FIG. 9. Higher performances (conversion, yield of isomers and selectivities) were obtained for the pillared materials of the invention. In particular, the activity of the stabilized sample was significantly improved compared with non stabilized counterparts.

TABLE 17

Results obtained at maximum isomerization conversion over some zeolites, an Al-pillared saponite (AlP—S), and over Al-pillared micas (samples F) and Al-pillared vermiculites (samples S).

| Catalyst 1% Pt | Si/Al | T max iso (° C.) | Total conv (%) | Yiso i-C8 (%) | Ycr (%) | Sel. i-C8 (%) | Mono- iso (%) | Di- iso (%) | 2MC7/ 3MC7 |
|---|---|---|---|---|---|---|---|---|---|
| CBV | 2.6 | 246 | 76.5 | 62.7 | 13.9 | 81.9 | 69.6 | 30.4 | 0.86 |
| CBV | 2.6 | 182 | 68.3 | 51.8 | 16.5 | 75.8 | 68.4 | 31.6 | 0.91 |
| CVB | 2.8 | 215 | 80.5 | 63.7 | 16.6 | 79.1 | 65.5 | 34.5 | 0.83 |
| CVB | 13.0 | 220 | 83.4 | 66.9 | 16.6 | 80.2 | 62.2 | 37.8 | 0.84 |
| CVB | 21.0 | 267 | 79.8 | 67.2 | 12.7 | 84.1 | 66.2 | 33.8 | 0.82 |
| CVB | 30.0 | 270 | 76.7 | 61.5 | 16.2 | 78.9 | 72.2 | 27.8 | 0.82 |
| CVB | 37.1 | 269 | 80.2 | 67.1 | 13.1 | 83.7 | 68.1 | 31.9 | 0.81 |
| ZB-75 | 37.5 | 212 | 79.2 | 68.3 | 10.9 | 86.3 | 68.2 | 31.8 | 0.89 |
| ZB-25 | 13.2 | 194 | 84.7 | 71.0 | 13.7 | 83.8 | 61.5 | 38.5 | 0.88 |
| AlP—S | | 244 | 83.7 | 67.8 | 16.0 | 81.0 | 66.2 | 33.8 | 0.85 |
| 1F029 | | 242 | 87.9 | 78.7 | 9.2 | 89.6 | 62.3 | 37.7 | 0.85 |
| 6F010 | | 238 | 85.6 | 79.1 | 6.5 | 92.4 | 64.1 | 36.0 | 0.86 |
| 1F041 | | 241 | 86.4 | 79.1 | 7.4 | 91.5 | 63.8 | 36.2 | 0.85 |
| 2F045 | | 238 | 88.0 | 80.0 | 7.9 | 91.0 | 65.8 | 34.2 | 0.85 |
| 2F047 | | 246 | 83.6 | 76.8 | 6.9 | 91.8 | 65.8 | 34.2 | 0.85 |
| 1S044 | | 241 | 87.8 | 78.9 | 8.9 | 89.9 | 62.3 | 37.7 | 0.85 |
| 3S037 | | 222 | 86.9 | 80.2 | 6.7 | 92.3 | 62.4 | 37.6 | 0.88 |
| 3S044* | | 207 | 89.5 | 83.3 | 6.2 | 93.1 | 59.7 | 40.3 | 0.90 |

*stabilized

A duration test was performed over a stabilized Pt-impregnated (0.5 wt % Pt) Al-pillared mica at 207° C. and WHSV of 0.92 h$^{-1}$. After 190 h time on stream, no deactivation was noticed, with a total average conversion of 88.2% and yield of C8 isomers of 82.8% (selectivity of 93.9%).

Reduction of NO by $NH_3$

Figure 10:
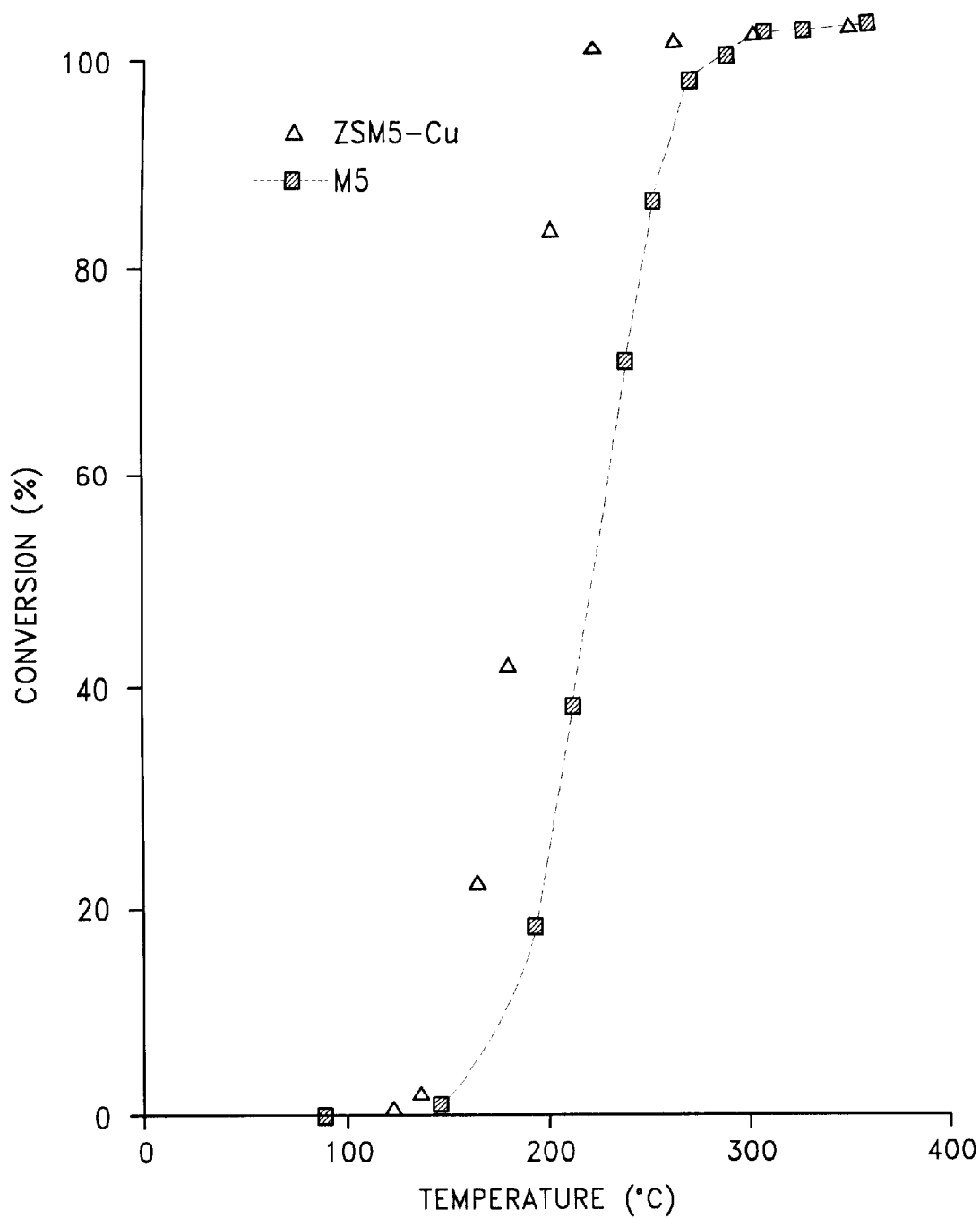
FIG. 10 represents reduction of NOx: variation of the conversion of NOx to N2 vs reaction temperature on Cu-ZSM-5 zeolite and Cu-exchanged Al-pillared mica.

A sample of pillared mica and a commercial zeolite ZSM-5 (SM-27, Si/Al=12–13.5, from VAW Aluminium AG) were twice Cu-exchanged with 2 M solution of copper nitrate at 80° C. for 1 h, and removal of excess salt. The catalytic tests were carried out in a fixed-bed microreactor on 50 mg samples diluted in small-sized quartz. The catalysts were heated at 90° C. for 2 h in flowing dry air. The reaction conditions were as follows: total flow: 200 ml min$^{-1}$ (40 ml min$^{-1}$ of NO, 5.000 ppm in He; 56 ml min$^{-1}$ NH$_3$, 5.000 ppm in He; and air=104 ml min$^{-1}$ (10.5% O$_2$ vol/vol). WHSV was 0.18 g NO g cata$^{-1}$ h$^{-1}$. On-line gas phase analysis was done in a Rotork Chemiluminescence NO$_x$ Analyzer. The experimental values were taken at stabilized conversions. The comparative results are shown in FIG. 10. Both Cu-ZSM-5 and Cu-Al-pillared mica (M5) exhibited similar performances, total reduction of NO being attained at about 200° C. in the zeolite and at above 300° C. for the Cu-exchanged Al-pillared mica.

REFERENCES

1. Rich, C. I., Soil Sci. Soc. Am. Proc. 24, 26, 1960.
2. Hsu, P. H. and Bates, T. F., Soil Sci. Soc. Am. Proc. 28, 763, 1964.
3. Brydon, J. E. and Turner, R. C., Clays Clay Miner. 20, 1, 1977.
4. Barnishel, R. I., in Minerals in Soil Environments, Soil Sci. Soc. Amer., Madison, p.331, 1977.
5. Schutz, A. and Poncelet, G., unpublished results
6. Hsu, P. H., Clays Clay Miner. 40, 300, 1992.
7. d'Espinose de la Caillerie, J. B. and Fripiat, J. J., Clay Miner. 29, 133, 1994.
8. Michot, L. J. et al., Clay Miner. 29, 133, 1994.
9. Vaughan, D. E. W., and Lussier, R. J., Proc. 5th Zeolite Conf., L. V. Rees (Ed.), Heyden & Sons, 94, 1980.
10. Akitt, J. W. et al., J. Chem. Soc., Dalton Trans. 604, 1972
11. Bottero, J. Y. et al., J. Phys. Chem. 84, 2933, 1980
12. Lahav, N. et al., Clays Clay Miner. 26, 107, 1978.
13. Schutz, A. et al., J., Clays Clay Miner. 35, 251, 1987.
14. Zhonghua, G. et al., Microporous Mater., 3, 165, 1994.
15. Bergaoui, L. et al., Chem. Soc. Faraday Trans. 91, 2229, 1995.
16. de Boer, J. H. and Broekhoff, J. C. P., J. Catal. 10, 391, 1968.
17. Remy, M. J. et al., Microporous Mater. 7(6), 287, 1996.
18. Sing, K. S. W. et al., Pure Appl. Chem. 57, 603, 1985.
19. Moreno, S. et al., J. Catal. 162, 198, 1996.

What is claimed is:

1. Pillared vermiculites precalcined or not and/or trioctahedral micas obtained according to the process comprising: conditioning the micas and/or vermiculites through accelerated weathering so as to partially reduce the layer charge of the micas and/or vermiculites, wherein conditioning the micas and/or vermiculites comprises successive steps as follows:
   a) treating the micas and/or vermiculites with a solution of an acid;
   b) calcining the product recovered from step a) at about 600° C. for approximately 4 hours under static air; and
   c) treating the product from step b) with a solution of a salt of a hydrated cation until exchange is completed;
   and pillaring the charge-reduced micas and/or vermiculites, wherein the pillared vermiculites exhibit basal spacings above 16 Å.

2. The pillared vermiculites according to claim 1, wherein said spacings are above 17 Å.

3. The pillared vermiculites according to claim 1, wherein said spacings are above 18 Å.

4. Pillared trioctahedral micas according to claim 1, wherein said micas exhibit surface areas of 145 to 365 m$^2$ g$^{-1}$, micropore volumes of 0.036 to 0.129 ml g$^{-1}$ and a total pore volume of 0.073 to 0.268 ml g$^{-1}$.

5. Pillared precalcined vermiculites according to claim 1, wherein said vermiculites exhibit surface areas of 121 to 192 m$^2$ g$^{-1}$, micropore volumes of 0.041 to 0.066 ml g$^{-1}$ and a total pore volume of 0.1 18 to 0.177 ml g$^{-1}$.

6. The pillared vermiculites according to claim 1 in admixture or in combination with other catalytic systems as zeolites, oxides, and mixed oxides.

7. The pillared vermiculites according to claim 1 supporting metals or metal oxides or metal compounds.

8. The pillared vermiculites according to claim 1, wherein a chemical structure is modified with other phosphorus and sulfur compounds.

9. A process for proton catalyzed reaction of hydrocarbons comprising flowing a mixture of said hydrocarbons and hydrogen in the vapor phase over the pillared vermiculites of claim 1.

10. A process for N$_x$, abatement comprising flowing a mixture of said NO$_x$ and ammonia gas over the pillared vermiculites of claim 1.

* * * * *